US011400063B2

(12) United States Patent
Tardif

(10) Patent No.: US 11,400,063 B2
(45) Date of Patent: Aug. 2, 2022

(54) EARLY ADMINISTRATION OF LOW-DOSE COLCHICINE AFTER MYOCARDIAL INFARCTION

(71) Applicant: INSTITUT DE CARDIOLOGIE DE MONTREAL, Montreal (CA)

(72) Inventor: Jean-Claude Tardif, Montreal (CA)

(73) Assignee: INSTITUT DE CARDIOLOGIE DE MONTREAL, Montreal (CA)

( * ) Notice: Subject to any disclaimer, the term of this patent is extended or adjusted under 35 U.S.C. 154(b) by 0 days.

(21) Appl. No.: 17/097,285

(22) Filed: Nov. 13, 2020

(65) Prior Publication Data

US 2021/0145773 A1 May 20, 2021

Related U.S. Application Data

(60) Provisional application No. 63/093,988, filed on Oct. 20, 2020, provisional application No. 62/935,865, filed on Nov. 15, 2019.

(51) Int. Cl.
*A61K 31/165* (2006.01)
*A61P 9/10* (2006.01)

(52) U.S. Cl.
CPC ............. *A61K 31/165* (2013.01); *A61P 9/10* (2018.01)

(58) Field of Classification Search
CPC .................................................. A61K 31/165
See application file for complete search history.

(56) References Cited

U.S. PATENT DOCUMENTS 10,265,281 B2    4/2019  Nidorf

FOREIGN PATENT DOCUMENTS

WO    WO-2014/066944 A1    5/2014

OTHER PUBLICATIONS

Akodad et al., "Interest of colchicine in the treatment of acute myocardial infarct responsible for heart failure in a mouse model," Int J Cardiol. 240:347-353 (2017).
Bouabdallaoui et al., "Time-to-treatment initiation of colchicine and cardiovascular outcomes after myocardial infarction in the Colchicine Cardiovascular Outcomes Trial (COLCOT)," Eur Heart J. 00:1-8 (2020).
Deftereos et al., "Anti-Inflammatory Treatment with Colchicine in Acute Myocardial Infarction: A Pilot Study," Circulation 132(15):1395-403 (2015).
Hennessy et al., "The Low Dose Colchicine after Myocardial Infarction (LoDoCo-MI) study: A pilot randomized placebo controlled trial of colchicine following acute myocardial infarction," Am Heart J. 215:62-69 (2019).
Newby et al., "Inflammation as a Treatment Target after Acute Myocardial Infarction," N Engl J Med. 381(26):2562-2563 (2019).
Nidorf et al., "Low-dose colchicine for secondary prevention of cardiovascular disease," J Am Coll Cardiol. 61 (4):404-410 (2013).
Nidorf et al., "Why Colchicine Should Be Considered for Secondary Prevention of Atherosclerosis: An Overview," Clin Ther. 41(1):41-48 (2019).
Tardif et al., "Efficacy and Safety of Low-Dose Colchicine after Myocardial Infarction," N Engl J Med. 381(26):2497-2505 (2019).
Tucker et al., "Colchicine as a Novel Therapy for Suppressing Chemokine Production in Patients with an Acute Coronary Syndrome: A Pilot Study," Clin Ther. 41(10):2172-2181 (2019).
Vaidya et al., "Colchicine Therapy and Plaque Stabilization in Patients with Acute Coronary Syndrome: ACT Coronary Angiography Study," JACC Cardiovasc Imaging. 11 (2 PT 2):305-316 (2018).
Vaidya et al., "The Role of Colchicine in Acute Coronary Syndromes," Clin Ther. 41 (1): 11-20 (2018).
Office Action for Canadian Patent Application No. 3,099,143 dated Mar. 5, 2021 (6 pages).
Montreal Heart Institute, "Colchicine Cardiovascular Outcomes Trial (COLCOT) (COLCOT)", U.S. National Library of Medicine, NCT02551094, dated Sep. 16, 2015 (9 pages).
Office Action for Canadian Patent Application No. 3,099,143 dated Sep. 16, 2021 (4 pages).

*Primary Examiner* — Brian J Davis
(74) *Attorney, Agent, or Firm* — Clark & Elbing LLP

(57) ABSTRACT

The invention relates to colchicine for use in a method of treating a patient after having a myocardial infarction (MI), the method including initiating the administration of colchicine at a daily low dose to the patient within about 3 days of the MI.

50 Claims, 3 Drawing Sheets

EARLY ADMINISTRATION OF LOW-DOSE COLCHICINE AFTER MYOCARDIAL INFARCTION

BACKGROUND OF THE INVENTION

The invention relates to a treatment regimen for patients after suffering a myocardial infarction.

Inflammation appears to play an important role in atherosclerosis (Hansson G K, Inflammation, atherosclerosis, and coronary artery disease. *N Engl J Med* 2005; 352:1685-95). Inhibition of interleukin-1β by the injectable monoclonal antibody canakinumab led to a 15% lower risk of cardiovascular events than was observed with placebo in the Canakinumab Antiinflammatory Thrombosis Outcomes Study (CANTOS) but also led to a slightly higher incidence of fatal infections (Ridker P M et al., Antiinflammatory therapy with canakinumab for atherosclerotic disease. *N Engl J Med* 2017; 377:1119-31). In contrast, methotrexate did not affect cardiovascular outcomes or plasma markers of inflammation in the Cardiovascular Inflammation Reduction Trial (CIRT) (Ridker P M et al., Low-dose methotrexate for the prevention of atherosclerotic events. *N Engl J Med* 2019; 380:752-62). Considering these differing results and given that canakinumab is not clinically available for cardiovascular prevention, the search for a widely used alternative antiinflammatory treatment that may reduce the risk of atherosclerotic events among patients with coronary artery disease continues.

Colchicine is an inexpensive, orally administered, potent anti-inflammatory medication that was initially extracted from the autumn crocus and has been used for centuries. Its mechanism of action is through the inhibition of tubulin polymerization and microtubule generation and, possibly, effects on cellular adhesion molecules, inflammatory chemokines, and the inflammasome (Ravelli R B et al., Insight into tubulin regulation from a complex with colchicine and a stathmin-like domain. *Nature* 2004; 428:198-202; Perico N et al., Colchicine interferes with L-selectin and leukocyte function-associated antigen-1 expression on human T lymphocytes and inhibits T cell activation. *J Am Soc Nephrol* 1996; 7:594-601; Pope R M and Tschopp J, The role of interleukin-1 and the inflammasome in gout: implications for therapy. *Arthritis Rheum* 2007; 56:3183-8). Colchicine is currently indicated for the treatment of gout, familial Mediterranean fever, and pericarditis (Cerquaglia C et al., Pharmacological and clinical basis of treatment of Familial Mediterranean Fever (FMF) with colchicine and analogues: an update. *Curr Drug Targets Inflamm Allergy* 2005; 4:117-24; and Imazio M et al., Colchicine in addition to conventional therapy for acute pericarditis: results of the COlchicine for acute PEricarditis (COPE) trial. *Circulation* 2005; 112:2012-6).

In the Low-Dose Colchicine (LoDoCo) trial, patients with stable coronary disease treated with colchicine at a dose of 0.5 mg once daily had fewer cardiovascular events than those not receiving colchicine (Nidorf S M et al., Low-dose colchicine for secondary prevention of cardiovascular disease. *J Am Coll Cardiol* 2013; 61:404-10). However, that trial enrolled only 532 patients and was not placebo-controlled.

Because acute coronary syndromes are associated with higher risks of recurrent events and exacerbated inflammation a need exists in the art for new treatment regimens.

SUMMARY OF THE INVENTION

A clinical trial referred to as the Colchicine Cardiovascular Outcomes Trial (COLCOT) was conducted to evaluate the effects of colchicine on cardiovascular outcomes as well as its long-term safety profile in patients who had recently had a myocardial infarction.

The results of the COLCOT trial support that the use of colchicine in patients who have recently had a myocardial infarction significantly improved their quality of life in several ways. Colchicine at a daily low dose of 0.5 mg led to a statistically significant lower risk of ischemic cardiovascular events than placebo. Death from cardiovascular causes, resuscitated cardiac arrest, myocardial infarction, stroke, and urgent hospitalization for angina leading to coronary revascularization was also significantly lower among the patients who received 0.5 mg of colchicine than those who received placebo. Patients receiving low dose colchicine had reduced morbidity relative to placebo, as is demonstrated by the rates of the respective primary composite end points for the two patient populations (P=0.02). This reduction in morbidity was particularly prominent among colchicine-receiving patients in the reduction of severe conditions, such as stroke and urgent hospitalization for angina leading to revascularization: hazard ratios are 0.26 (95% confidence interval is 0.10-0.70) and 0.50 (95% confidence interval is 0.31-0.81), respectively. Still further, unlike the use of the anti-inflammatory canakinumab for atherosclerotic events, colchicine did not increase the incidence of septic shock. Moreover, no serious adverse event of myopathy linked to colchicine occurred despite the use of statins in 99% of trial participants.

The results of the COLCOT trial have been further analyzed to determine if time to treatment initiation (TTI) had any effect on the outcome of the treatment. Three different cutoffs for TTI were used in order to determine the association between early initiation of therapy and clinical outcomes. These cutoffs were determined based on the usual journey of patients with MI. The first 30-day post-MI timeline was divided into three independent periods of time, and analyzed as such: from day 0 to 3, referring to in-hospital management; from day 4 to 7, referring to early post-discharge period and from day 8 to 30, referring to late post-discharge period.

The main COLCOT results revealed that colchicine reduced the risk of ischemic CV events by 23% in the post-MI setting. Results from the present TTI analysis support that early suppression of inflammation after MI provides even greater benefits, with a reduction of 48% in the risk of the composite primary endpoint when colchicine was initiated between days 0 and 3. The demonstrated cost-effectiveness of low-dose colchicine also supports its large-scale use after MI. Results of the LoDoCo2 study of patients with stable coronary artery disease complement those of COLCOT in the post-MI setting.

In view of the aforementioned, the invention, in one aspect, relates to colchicine for use in a method of treating a patient after having a myocardial infarction (MI), the method comprising initiating the administration of colchicine at a daily low dose to the patient within about 3 days of the MI.

In another aspect, the invention relates to a colchicine for use in a method of treating a patient after having a MI, the method comprising initiating the administration of colchicine at a daily low dose to the patient within about 4 days of the MI.

In another aspect, the invention relates to a colchicine for use in a method of treating a patient after having a MI, the method comprising initiating the administration of colchicine at a daily low dose to the patient within about 5 days of the MI.

In another aspect, the invention relates to a colchicine for use in a method of treating a patient after having a MI, the method comprising initiating the administration of colchicine at a daily low dose to the patient within about 30 days of the MI.

In another aspect, the invention relates to a method of treating a patient after having a MI, the method comprising initiating the administration of colchicine at a daily low dose to the patient within about 3 days of the MI.

In another aspect, the invention relates to a method of treating a patient after having a MI, the method comprising initiating the administration of colchicine at a daily low dose to the patient within about 4 days of the MI.

In another aspect, the invention relates to a method of treating a patient after having a MI, the method comprising initiating the administration of colchicine at a daily low dose to the patient within about 5 days of the MI.

In another aspect, the invention relates to a method of treating a patient after having a MI, the method comprising initiating the administration of colchicine at a daily low dose to the patient within about 30 days of the MI.

In another aspect, the invention relates to the use of a daily low dose of colchicine for treating a patient after having a MI, wherein the use is initiated within about 3 days of the MI.

In another aspect, the invention relates to the use of a daily low dose of colchicine for treating a patient after having a MI, wherein the use is initiated within about 4 days of the MI.

In another aspect, the invention relates to the use of a daily low dose of colchicine for treating a patient after having a MI, wherein the use is initiated within about 5 days of the MI.

In another aspect, the invention relates to the use of a daily low dose of colchicine for treating a patient after having a MI, wherein the use is initiated within about 30 days of the MI.

In a further aspect, the invention relates to the use of colchicine for the manufacture of a medicament for treating a patient after having a MI, wherein the colchicine is a low dose colchicine for daily administration initiated within about 3 days of the MI.

In a further aspect, the invention relates to the use of colchicine for the manufacture of a medicament for treating a patient after having a MI, wherein the colchicine is a low dose colchicine for daily administration initiated within about 4 days of the MI.

In a further aspect, the invention relates to the use of colchicine for the manufacture of a medicament for treating a patient after having a MI, wherein the colchicine is a low dose colchicine for daily administration initiated within about 5 days of the MI.

In a further aspect, the invention relates to the use of colchicine for the manufacture of a medicament for treating a patient after having a MI, wherein the colchicine is a low dose colchicine for daily administration initiated within about 30 days of the MI.

In another aspect, the present invention relates to low-dose colchicine for use in treating a patient having a MI, wherein the colchicine is for daily administration initiated within about 3 days of the MI.

In another aspect, the present invention relates to low-dose colchicine for use in treating a patient having a MI, wherein the colchicine is for daily administration initiated within about 4 days of the MI.

In another aspect, the present invention relates to low-dose colchicine for use in treating a patient having a MI, wherein the colchicine is for daily administration initiated within about 5 days of the MI.

In another aspect, the present invention relates to low-dose colchicine for use in treating a patient having a MI, wherein the colchicine is for daily administration initiated within about 30 days of the MI.

In some embodiments, the method involves administering colchicine within 5 days of the MI (for example, at 1 day, 2 days, 3 days, or 4 days). In some embodiments, the method includes administering colchicine within 4 days of the myocardial infarction (for example, at 1 day, 2 days, or 3 days). In still other embodiments, the method includes administering colchicine within 3 days of the myocardial infarction (for example, at 1 day or 2 days).

In some embodiments, the patient administered colchicine received percutaneous coronary intervention for treating the patient's myocardial infarction.

In some embodiments, the myocardial infarction is acute MI (AMI). In some embodiments, the MI is not type 2 MI.

In some embodiments, the patient administered was previously prescribed a medication (for example, an antiplatelet agent, a statin, aspirin or a combination thereof).

In some embodiments, the patient administered is concurrently being treated with a medication (for example, an antiplatelet agent, a statin, aspirin, or a combination thereof).

In some embodiments, the patient is at a lower risk of a cardiovascular event, relative to a patient not being administered colchicine. For example, the cardiovascular event is an ischemic cardiovascular event. In some embodiments, the cardiovascular event is cardiovascular death, resuscitated cardiac arrest, myocardial infarction, stroke, or urgent hospitalization for angina requiring coronary revascularization.

In some embodiments, the patient has atherosclerotic coronary artery disease.

In some embodiments the patient does not have severe heart failure, reduced left ventricular fraction, recent stroke, type 2 MI, planned coronary artery bypass by graft (CABG), inflammatory bowel disease or chronic diarrhea.

In another aspect, the invention relates to a method of reducing the risk of or preventing a stroke in a patient after having an MI, the method comprising initiating the administration of colchicine at a daily low dose to the patient within about 30 days of an MI.

In some embodiments, the method involves administering colchicine within 4-7 days (for example, 5 days, 6 days, or 7 days) of the MI.

In some embodiments, the method involves administering colchicine within 3 days of the MI.

In another aspect, the invention relates to the use of a daily low dose of colchicine for reducing the risk of or preventing a stroke in a patient after having a MI, wherein the use is initiated within 30 days of the MI.

In another aspect, the invention relates to the use of a daily low dose of colchicine for reducing the risk of or preventing a stroke in a patient after having a MI, wherein the use is initiated between 4-7 days after the MI.

In some embodiments, the invention relates to the use of a daily low does of colchicine for reducing the risk of or preventing a stroke in a patient after having a MI, wherein the use is initiated within 3 days of the MI.

In a further aspect, the invention relates to the use of colchicine for the manufacture of a medicament for reducing the risk of or preventing a stroke in a patient after having a MI, wherein the colchicine is a low dose colchicine for daily administration initiated within 30 days of the MI.

In a further aspect, the invention relates to the use of colchicine for the manufacture of a medicament for reducing the risk of or preventing a stroke in a patient after having a MI, wherein the colchicine is a low dose colchicine for daily administration initiated between 4 and 7 days of the MI.

In another aspect, the present invention relates to the use of colchicine for the manufacture of a medicament for reducing the risk of or preventing stroke in a subject after having a MI, wherein the colchicine is for daily administration initiated within about 3 days of the MI.

In some embodiments, the administration of colchicine is initiated upon assessment in (a) an emergency department (ED), (b) the hospital, or (c) a medical office setting.

In some embodiments, colchicine is administered in the form of a tablet or a capsule (e.g., a coated tablet or capsule). In some embodiment, colchicine is administered in the form of a film-coated tablet.

In some embodiments, colchicine is administered at 0.3 to 0.7 mg. For example, colchicine is administered at 0.4 to 0.6 mg, and is preferably administered at about 0.5 mg. In some embodiments, colchicine is administered in a 0.5 mg tablet or a 0.6 mg tablet. In other embodiments, colchicine is administered in a 0.25 mg tablet.

In some embodiments, colchicine is administrated once, twice, or three times daily.

In some embodiments, colchicine is administered once per day.

In some embodiments, the colchicine is administered without pre-loading the patient with colchicine (e.g., administering a higher dose, such as 1.0 mg per day or higher (1.5 mg or 2.0 mg) in a single or multiple doses, at the onset of the treatment for one, two, or three days before switching to a lower dose of, e.g., 0.5 mg per day, for the remainder of the duration of treatment).

In some embodiments, the patient is an adult human (i.e., the patient is 18 years old or older).

In another aspect, the invention relates to colchicine for use in a method of treating a patient after having a myocardial infarction (MI), the method including the administration of colchicine at a daily low dose to the patient within about 3 days (e.g., 1 day, 2 days, and 3 days) of the MI.

Use of colchicine for treating a patient after having a myocardial infarction typically continues, as needed, throughout the life of a patient. For example, in some embodiments, the duration of treatment is for 6 months, 12 months, 18 months, 24 months, 30 months, 36 months, or even longer as is needed. In some embodiments, the duration of the treatment is for at least about 23 months.

Various colchicine formulations, including film-coated tablets, are readily available and well known in the art.

Other features and advantages of the invention will be apparent from the following Detailed Description, the Drawings, and the Claims.

Definitions

As used herein, the term "cardiovascular death" refers to death resulting from a cardiovascular disease, including coronary heart disease, cerebrovascular disease, peripheral arterial disease, rheumatic heart disease, congenital heart disease, deep vein thrombosis, or a pulmonary embolism, or sudden cardiac event, including cardiac arrest and myocardial infarction.

As used herein, the term "myocardial infarction" refers to a cardiovascular disorder characterized by localized necrosis resulting from obstruction of the blood supply. MI may be classified as an ST elevation myocardial infarction (STEMI) or Non-ST elevation myocardial infarction (NSTEMI) based on the results of an ECG. A more explicit classification system, based on international consensus in 2012, also exists. This classifies myocardial infarctions into five types including types 1 and 2. Type-1 AMI is caused by an acute atherothrombotic coronary event; type-2 AMI is a more heterogeneous entity, where a condition other than coronary artery disease (CAD) contributes to an acute imbalance between oxygen supply (e.g., hypoxemia, anemia, hypotension) and demand (e.g., tachycardia, hypertension).

As used herein, the term "resuscitated cardiac arrest" refers an abrupt loss of heart function resulting in a loss of blood flow to the body which requires the subject be resuscitated using any method known to one of skill in the art, including cardiopulmonary resuscitation or a defibrillator.

As used herein, the term "urgent hospitalization for angina requiring coronary revascularization" refers to an immediate need for a patient to be hospitalized due to severe chest discomfort felt due to ischemic heart disease which requires surgical intervention grafting and/or stenting approaches to improving blood flow to the heart and relieve angina.

As used herein, the term "stroke" refers to a condition which occurs when the blood supply to a part of the brain is suddenly interrupted (i.e., ischemic stroke) or when a blood vessel in the brain bursts and releases blood into the spaces surrounding the brain cells (i.e., hemorrhagic stroke). The symptoms of a stroke include numbness or weakness, especially on one side of the body corresponding to the contralateral side of the stroke, confusion, trouble understanding or producing speech, impaired vision in both eyes, impaired mobility, dizziness, or loss of balance or coordination. Stroke may be diagnosed using several techniques, such as, e.g., neurological examination, blood testing, computed tomography (CT) scan, magnetic resonance imaging (MRI) scan, Doppler ultrasound, and arteriography. Although stroke is a disease of the brain, it can affect the entire body by causing, e.g., paralysis, cognitive impairment, speech impairment, emotional dysregulation, and pain.

DETAILED DESCRIPTION OF THE INVENTION

Figure 1:
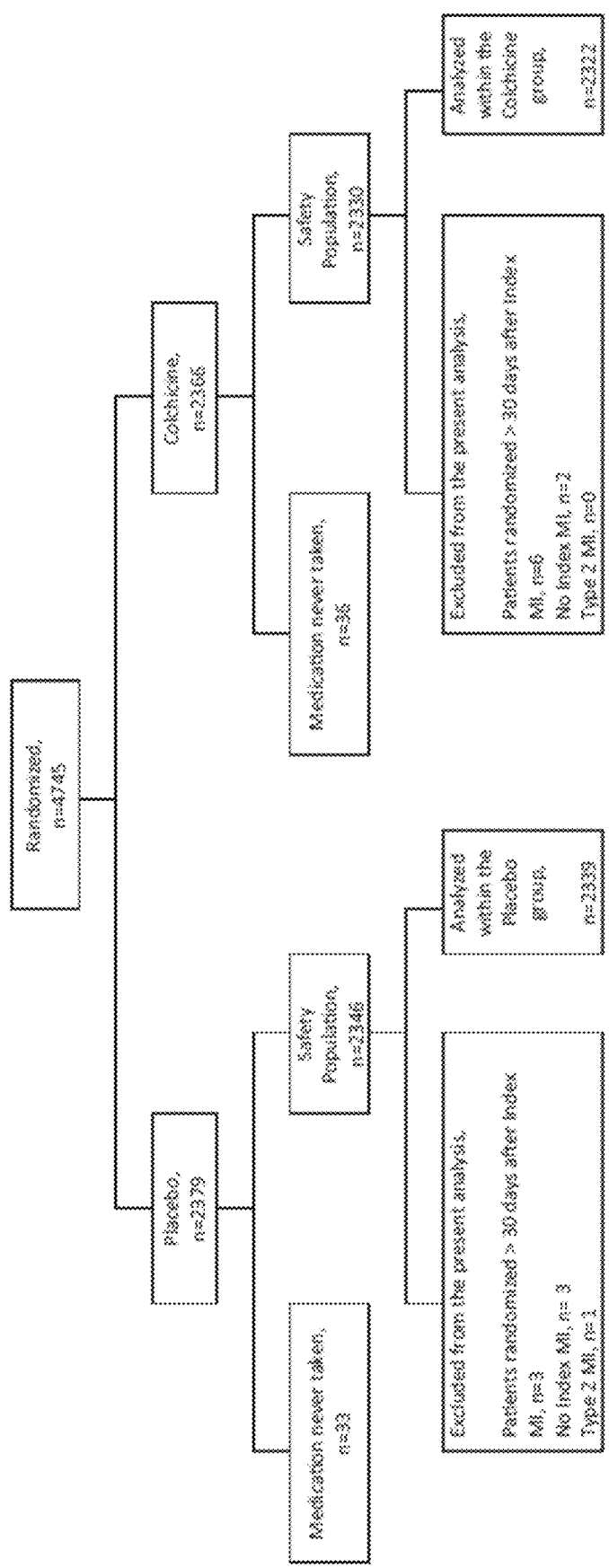
FIG. 1 is a schematic of a flow chart of the randomization and subject disposition of the patients in the Time-to-Treatment study.

We performed a randomized, double-blind trial involving patients recruited within 30 days after a myocardial infarction. The patients were randomly assigned to receive either low-dose colchicine (0.5 mg once daily) or placebo. A total of 4745 patients were enrolled; 2386 patients were assigned to the colchicine group, and 2379 to the placebo group. Patients were followed for a median of 22.6 months.

The primary efficacy end point was a composite of death from cardiovascular causes, resuscitated cardiac arrest, myocardial infarction (e.g., acute myocardial infraction or type II myocardial infarction), stroke, or urgent hospitalization for angina leading to coronary revascularization. The components of the primary end point and safety were also assessed.

Study Design and Patient Population

COLCOT was an international multicenter, randomized, double-blinded trial that randomly assigned patients to receive either low-dose colchicine (0.5 mg once daily) or placebo. The study protocol and main results have been published (see, Tardif et al., N Engl J Med 2019). Patients were considered eligible if they had a recent MI (<30 days). Main exclusion criteria were severe heart failure, reduced left ventricular ejection fraction (<35%), recent stroke (<3 months), type 2 MI, recent (<3 years) or planned coronary artery bypass graft (CABG), history of cancer (<3 years), and inflammatory bowel disease or chronic diarrhea. All patients enrolled in the trial benefited from percutaneous coronary intervention whenever indicated and guidelines-directed management of CV disease prior to randomization (see. Tardif et al., N Engl J Med 2019).

Clinical follow-up consisted of evaluations at 1 and 3 months after randomization and every 3 months thereafter. An independent clinical endpoint committee, blinded to trial-group assignment, adjudicated clinical endpoints. The trial was locally approved by the various institutional review boards, and all patients signed a written informed consent before enrollment.

Efficacy Endpoints

The primary efficacy endpoint was a composite of CV death, resuscitated cardiac arrest, MI, stroke, or urgent hospitalization for angina requiring coronary revascularization. The secondary endpoints consisted of the components of the primary efficacy endpoint, all-cause death, and a composite of CV death, resuscitated cardiac arrest, MI, or stroke. Exploratory endpoints included all coronary revascularizations, including both elective and urgent coronary revascularizations.

Cutoffs for Time-to-Treatment Initiation (TTI) of Colchicine

Three different cutoffs for TTI were used in order to determine the association between early initiation of therapy and clinical outcomes. These cutoffs were determined based on the usual journey of patients with MI. The first 30-day post-MI timeline was divided into three independent periods of time, and analyzed as such: from day 0 to 3, referring to in-hospital management; from day 4 to 7, referring to early post-discharge period and from day 8 to 30, referring to late post-discharge period.

Results

Baseline Characteristics for Patients in TTI Analysis

Of the 4745 patients randomized in COLCOT, 4661 were included in the TTI analysis (colchicine, N=2322; placebo, N=2339) (FIG. 1). Overall, patients were randomized at 13.510.1 days following the index MI, 25.6% between days 0 and 3, 15.4% between days 4 and 7 and 59.0% at day 8 or after. Baseline characteristics were similar between the colchicine and placebo groups (Table 1). Patients were mostly men (81.0%) with a mean age of 60.5 years, 20.2% had diabetes, 51.0% had a history of hypertension, 29.7% were active smokers, and 16.8% had had a prior PCI. Background therapy included aspirin, a second anti-platelet agent and a statin in 98.8%, 98.0% and 99.0% of patients, respectively. The vast majority of patients (93.0%) underwent percutaneous coronary intervention (PCI) during the index hospitalization, with no difference in terms of time to PCI between the two groups.

TABLE 1

Baseline Characteristics according to treatment allocation for Time-to-Treatment Initiation (TTI)

| Characteristics | All patients N = 4661 | Colchicine group N = 2322 | Placebo group N = 2339 |
| --- | --- | --- | --- |
| Age (years)-mean ± SD | 60.5 ± 10.6 | 60.6 ± 10.6 | 60.5 ± 10.6 |
| Male sex-no. (%) | 3774 (81.0%) | 1861 (80.1%) | 1913 (81.8%) |
| BMI (kg/m$^2$)-mean ± SD | 28.3 ± 4.7 | 28.2 ± 4.8 | 28.4 ± 4.7 |
| Current Smoking-no./total no. (%) | 1382/4659 (29.7) | 694/2322 (29.9%) | 688/2337 (29.4%) |
| History of Hypertension-no. (%) | 2377 (51.0%) | 1160 (50.0%) | 1217 (52.0%) |
| History of Diabetes-no. (%) | 942 (20.2%) | 451 (19.4%) | 491 (21.0%) |
| Prior MI-no. (%) | 751 (16.1%) | 360 (15.5%) | 391 (16.7%) |
| Prior PCI-no. (%) | 783 (16.8%) | 382 (16.5%) | 401 (17.1%) |
| Prior CABG-no. (%) | 146 (3.1%) | 66 (2.8%) | 80 (3.4%) |
| Prior HF-no. (%) | 90 (1.9%) | 48 (2.1%) | 42 (1.8%) |
| Prior Stroke or TIA-no. (%) | 119 (2.6%) | 53 (2.3%) | 66 (2.8%) |
| PCI associated with the index event-no. (%) | 4336 (93.0%) | 2154 (92.8%) | 2182 (93.3%) |

TABLE 1-continued

Baseline Characteristics according to treatment allocation for Time-to-Treatment Initiation (TTI)

| Characteristics | All patients N = 4661 | Colchicine group N = 2322 | Placebo group N = 2339 |
|---|---|---|---|
| Medication use-no. (%): | | | |
| Aspirin | 4605 (98.8%) | 2291 (98.7%) | 2314 (98.9%) |
| Other antiplatelet agent | 4567 (98.0%) | 2267 (97.6%) | 2300 (98.3%) |
| Statin | 4615 (99.0%) | 2297 (98.9%) | 2318 (99.1%) |
| Beta-blocker | 4143 (88.9%) | 2077 (89.4%) | 2066 (88.3%) |
| TTI 0-3 days-no. (%) | 1193 (25.6%) | 604 (26.0%) | 589 (25.2%) |
| TTI 4-7 days-no. (%) | 720 (15.4%) | 364 (15.7%) | 356 (15.2%) |
| TTI ≥8 days-no. (%) | 2748 (59.0%) | 1354 (58.3%) | 1394 (59.6%) |
| Time from index MI to randomization (days)-mean ± SD | 13.5 ± 10.1 | 13.5 ± 10.1 | 13.5 ± 10.0 |
| Time from Index MI to PCI (days)-mean ± SD | 1.4 ± 2.9 | 1.4 ± 2.9 | 1.4 ± 2.9 |
| Time from PCI to randomization (days)-mean ± SD | 11.9 ± 9.9 | 11.9 ± 9.9 | 11.9 ± 9.9 |

Abbreviations: CABG, coronary-artery bypass graft surgery; HF, heart failure; PCI, percutaneous coronary intervention; TIA, transient ischemic attack.
Data were missing on the following characteristics: age (assessed according to date of birth; see below) for 431 patients (213 in the colchicine group and 218 in the placebo group) and body-mass index (the weight in kilograms divided by the square of the height in meters) for 5 (1 and 4 patients, respectively).
Date of birth was not required field because it was considered in some countries to be sensitive data that could allow for the identification of patients.
For statistical reporting, missing information regarding the day of birth was replaced by 15, and missing information regarding the month and day of birth was replaced by July 1.
Baseline characteristics according to TTI strata are shown in Table 2. Patients in whom therapy was initiated between days 0 and 3, when compared to those at days 8 to 30, were younger (59.1 ± 10.8 vs. 61.3 ± 10.4 years) and more often active smokers (43.8 vs. 20.2%), had less commonly hypertension (41.1 vs. 56.2%) and diabetes (17.4 vs. 22.0%) but underwent more often PCI associated with the index MI (95.8 vs. 91.3%), all $p < 0.05$.

TABLE 2

Baseline characteristics according to TTI

| Characteristics | TTI 0-3 days N = 1193 | TTI 4-7 days N = 720 | TTI ≥ 8 days N = 2748 | p* | p** |
|---|---|---|---|---|---|
| Age (years)-mean ± SD | 59.1 ± 10.8 | 60.1 ± 11.0 | 61.3 ± 10.4 | <0.0001 | <0.0001 |
| Male sex- no. (%) | 980 (82.2%) | 605 (84.0%) | 2189 (80.0%) | 0.014 | 0.071 |
| BMI (kg/m$^2$)-mean ± SD | 28.1 ± 4.6 | 27.7 ± 4.6 | 28.6 ± 4.8 | <0.0001 | 0.004 |
| Current Smoking-no. (%) | 522 (43.8%) | 306 (42.6%) | 554 (20.2%) | <0.0001 | <0.0001 |
| History of Hypertension-no. (%) | 490 (41.1%) | 343 (47.6%) | 1544 (56.2%) | <0.0001 | <0.0001 |
| History of Diabetes no. (%) | 208 (17.4%) | 130 (18.1%) | 604 (22.0%) | 0.001 | 0.001 |
| Prior MI-no. (%) | 170 (14.3%) | 111 (15.4%) | 470 (17.1%) | 0.070 | — |
| Prior PCI no. (%) | 182 (15.3%) | 107 (14.9%) | 494 (18.0%) | 0.035 | 0.037 |
| Prior CABG-no. (%) | 34 (2.9%) | 30 (4.2%) | 82 (3.0%) | 0.218 | — |
| Prior HF-no. (%) | 14 (1.2%) | 12 (1.7%) | 64 (2.3%) | 0.046 | 0.017 |
| Prior Stroke or TIA-no. (%) | 20 (1.7%) | 21 (2.9%) | 78 (2.8%) | 0.084 | — |
| PCI associated with the index event-no. (%) | 1143 (95.8%) | 685 (95.1%) | 2508 (91.3%) | <0.0001 | <0.0001 |
| Medication use-no. (%) | | | | | |
| Aspirin | 1181 (99.0%) | 715 (99.3%) | 2709 (98.6%) | 0.219 | — |
| Other antiplatelet agent | 1177 (98.7%) | 708 (98.3%) | 2682 (97.6%) | 0.072 | — |

TABLE 2-continued

Baseline characteristics according to TTI

| Characteristics | TTI 0-3 days N = 1193 | TTI 4-7 days N = 720 | TTI ≥ 8 days N = 2748 | p* | p** |
|---|---|---|---|---|---|
| Statin | 1188 (99.6%) | 708 (98.3%) | 2719 (98.9%) | 0.024 | 0.047 |
| Beta-blocker | 1093 (91.6%) | 642 (89.2%) | 2408 (87.6%) | 0.001 | 0.0003 |
| Time from index MI to randomization (days)-mean ± SD | 2.1 ± 0.8 | 5.1 ± 1.1 | 20.8 ± 6.6 | <0.0001 | <0.0001 |
| Time from Index MI to PCI (days)-mean ± SD | 0.4 ± 0.7 | 1.4 ± 1.8 | 1.8 ± 3.6 | <0.0001 | <0.0001 |
| Time from PCI to randomization (days)-mean ± SD | 1.6 ± 0.9 | 3.7 ± 1.9 | 18.8 ± 7.3 | <0.0001 | <0.001 |

Abbreviations: CABG, coronary-artery bypass graft surgery; HF, heart failure; PCI, percutaneous coronary intervention; TIA, transient ischemic attack.
Data were missing on the following characteristics: age (assessed according to date of birth; see below) for 431 patients (213 in the colchicine group and 218 in the placebo group) and body-mass index (the weight in kilograms divided by the square of the height in meters) for 5 (1 and 4 patients, respectively).
Date of birth was not a required field because it was considered in some countries to be sensitive data that could allow for the identification of patients. For statistical reporting, missing information regarding the day of birth was replaced by 15, and missing information regarding the month and day of birth was replaced by July 1.
*Group comparison TTI 0-3 vs. TTI 4-7 vs. TTI ≥ 8 days
**Group comparison TTI < 3 vs. TTI ≥ 8 days Effects of Time-to-Treatment Initiation on the Primary Efficacy Endpoint The effects of colchicine on the primary endpoint according to TTI are shown in Table 3 and FIG. 2. A primary endpoint event occurred in 4.3% of patients in the colchicine group, as compared to 8.3% of those in the placebo group when TTI was between days 0 and 3 (N=1193, HR=0.52, 95% CI 0.32-0.84, p=0.007, FIG. 3A). Corresponding rates were 6.0 and 5.9% when TTI was between days 4 and 7 (N=720) and 5.7 and 7.1% when TTI was on day 8 or after (N=2748), but these differences between groups did not reach statistical significance. Table 3 also shows the percentages of patients with events and the hazard ratios for the components of the primary endpoint, including CV death (HR=1.04, 95% CI 0.15-7.37), resuscitated cardiac arrest (HR=0.33, 95% CI 0.03-3.20), MI (HR=0.58, 95% CI 0.32-1.05), stroke (HR=0.21, 95% CI 0.02-1.81) and urgent hospitalization for angina requiring coronary revascularization (HR=0.35, 95% CI 0.14-0.88).

TABLE 3

Efficacy endpoints according to TTI (N = 4661, colchicine vs. placebo)

| Endpoints | TTI 0-3 days, N = 1193 Colchicine vs. placebo no. (%) HR (95% CI); p | TTI 4-7 days, N = 720 Colchicine vs. placebo no. (%) HR (95% CI); p | TTI ≥ 8 days, N = 2748 Colchicine vs. placebo no. (%) HR (95% CI); p |
|---|---|---|---|
| Primary composite endpoint | 26 (4.3%) vs. 49 (8.3%) 0.52 (0.32-0.84); p = 0.007 | 22 (6.0%) vs. 21 (5.9%) 0.96 (0.53-1.75); p = 0.896 | 77 (5.7%) vs. 99 (7.1%) 0.82 (0.61-1.11); p = 0.200 |
| CV death | 2 (0.3%) vs. 2 (0.3%) 1.04 (0.15-7.37); p = 0.970 | 2 (0.5%) vs. 4 (1.1%) 0.45 (0.08-2.46); p = 0.356 | 15 (1.1%) vs. 18 (1.3%) 0.89 (0.45-1.76); p = 0.734 |
| Resuscitated cardiac arrest | 1 (0.2%) vs. 3 (0.5%) 0.33 (0.03-3.20); p = 0.340 | 2 (0.5%) vs. 1 (0.3%) 1.90 (0.17-20.95); p = 0.600 | 2 (0.1%) vs. 2 (0.1%) 1.02 (0.14-7.22); p = 0.986 |
| MI | 17 (2.8%) vs. 29 (4.9%) 0.58 (0.32-1.05); p = 0.071 | 16 (4.4%) vs. 9 (2.5%) 1.67 (0.74-3.78); p = 0.218 | 52 (3.8%) vs. 59 (4.2%) 0.93 (0.64-1.35); p = 0.710 |
| Stroke | 1 (0.2%) vs. 5 (0.8%) 0.21 (0.02-1.81); p = 0.156 | 1 (0.3%) vs. 3 (0.8%) 0.28 (0.03-2.71); p = 0.272 | 2 (0.1%) vs. 11 (0.8%) 0.19 (0.04-0.84); p = 0.029 |
| Urgent hospitalization for angina requiring coronary revascularization | 6 (1%) vs. 17 (2.9%) 0.35 (0.14-0.88); p = 0.026 | 4 (1.1%) vs. 6 (1.7%) 0.63 (0.18-2.24); p = 0.476 | 15 (1.1%) vs. 26 (1.9%) 0.61 (0.32-1.16); p = 0.131 |
| Secondary Composite Endpoint | 20 (3.3%) vs. 36 (6.1%) 0.55 (0.32-0.95); p = 0.031 | 18 (4.9%) vs. 16 (4.5%) 1.04 (0.53-2.03); p = 0.919 | 67 (4.9%) vs. 77 (5.5%) 0.92 (0.66-1.28); p = 0.629 |
| All-cause death | 6 (1.0%) vs. 6 (1.0%) 1.03 (0.33-3.19); p = 0.962 | 8 (2.2%) vs. 7 (2.0%) 1.03 (0.37-2.84); p = 0.957 | 26 (1.9%) vs. 31 (2.2%) 0.90 (0.53-1.51); p = 0.684 |
| All Coronary Revascularizations | 33 (5.5%) vs. 51 (8.7%) 0.63 (0.40-0.97); p = 0.037 | 25 (6.9%) vs. 18 (5.1%) 1.41 (0.76-2.61); p = 0.275 | 72 (5.3%) vs. 94 (6.7%) 0.81 (0.59-1.10); p = 0.172 |

The effects of colchicine on the primary endpoint for a TTI of less than 4 days is shown in Table 4 and Table 5. The effects of colchicine on the primary endpoint for a TTI of less than 5 days is shown in Table 6 and Table 7. Both the TTI of less than 4 days and the TTI of less than 5 days was were calculated using a basic model (Table 4 and Table 6) as well as an adjusted model (Table 5 and Table 7) which is described below in the statistical analysis section. In all cases, the interaction p-value was not significant (p>0.05), meaning that the conclusion over Placebo vs. Colchicine group can be obtained directly from the respective p-values for HR. In other words, relationships within the placebo and colchicine groups with TTI are both linear/parallel and the interpretation is straightforward. For a TTI of 4 days or less, colchicine was shown to offer additional protection over the placebo in both the basic (Table 4 and Table 6) and the adjusted models (Table 5 and Table 7). The adjusted models resulted in a hazard ratio (HR) of 0.58 and a p value of 0.0126.

TABLE 4

Effect of Colchicine with TTI of < 4 days calculated using basic model

| DELAY BETWEEN RANDOMIZATION AND INDEX MI | POSITIVELY ADJUDICATED PRIMARY ENDPOINT | Placebo N = 2339 | Colchicine N = 2322 | All N = 4661 |
|---|---|---|---|---|
| [0-4] days | N | 712 | 768 | 1480 |
| | Yes | 54 (7.6%) | 34 (4.4%) | 88 (5.9%) |
| | No | 658 (92.4%) | 734 (95.6%) | 1392 (94.1%) |
| [5-30] days | n | 1627 | 1554 | 3181 |
| | Yes | 115 (7.1%) | 91 (5.9%) | 206 (6.5%) |
| | No | 1512 (92.9%) | 1463 (94.1%) | 2975 (93.5%) |

Cox Regression Model for Time to First Positively Adjudicated Primary Endpoint Including Treatment Group. Delay between randomization and index MI and Delay between randomization and index MI ×Randomized treatment group interaction

| Interaction Effect | P-value |
|---|---|
| Delay between randomization and index MI × Randomized intermittent group | 0.1501 |

| Delay between randomization and index MI | Effect | HR (95% CI) | P-value |
|---|---|---|---|
| [0-4] days | Colchicine vs. placebo | 0.57 (0.37; 0.87) | 0.0098 |
| [5-20] days | Colchicine vs. placebo | 0.83 (0.63; 1.09) | 0.1739 |

Notes: Model based on N = 4661 observations.
Deaths of undetermined cause were classified as CV deaths.

TABLE 5

Effect of Colchicine with TTI of < 4 days calculated using adjusted model

| DELAY BETWEEN RANDOMIZATION AND INDEX MI | POSITIVELY ADJUDICATED PRIMARY ENDPOINT | Placebo N = 2339 | Colchicine N = 2322 | All N = 4661 |
|---|---|---|---|---|
| [0-4] days | N | 712 | 768 | 1480 |
| | Yes | 54 (7.6%) | 34 (4.4%) | 88 (5.9%) |
| | No | 658 (92.4%) | 734 (95.6%) | 1392 (94.1%) |
| [5-30] days | n | 1627 | 1554 | 3181 |
| | Yes | 115 (7.1%) | 91 (5.9%) | 206 (6.5%) |
| | No | 1512 (92.9%) | 1463 (94.1%) | 2975 (93.5%) |

Cox Regression Model for Time to First Positively Adjudicated Primary Endpoint Including Treatment Group. Delay between randomization and index MI and Delay between randomization and index MI × Randomized treatment group interaction. Age at randomization (years). History of diabetes, Prior coronary revascularization (prior PCI or prior CABG) and Prior HeartFailure

| Interaction Effect | P-value |
|---|---|
| Delay between randomization and index MI × Randomized intermittent group | 0.1533 |

| Delay between randomization and index MI | Effect | HR (95% CI) | P-value |
|---|---|---|---|
| [0-4] days | Colchicine vs. placebo | 0.58 (0.36; 0.89) | 0.0126 |
| [5-20] days | Colchicine vs. placebo | 0.84 (0.64; 1.11) | 0.2120 |

Notes: Model based on N = 4661 observations.
Deaths of undetermined cause were classified as CV deaths.

TABLE 6

Effect of Colchicine with TTI of < 5 days calculated using basic model

| DELAY BETWEEN RANDOMIZATION AN INDEX MI | POSITIVELY ADJUDICATED PRIMARY PENDPOINT | Placebo N = 2339 | Colchicine N = 2322 | All N = 4661 |
|---|---|---|---|---|
| [0-5] days | N | 821 | 859 | 1680 |
| | Yes | 56 (6.8%) | 40 (4.7%) | 96 (5.7%) |
| | No | 765 (93.2%) | 819 (95.3%) | 1584 (94.3%) |
| [6-30] days | n | 1518 | 1463 | 2981 |
| | Yes | 113 (7.4%) | 85 (5.8%) | 198 (6.6%) |
| | No | 1405 (92.6%) | 1378 (94.2%) | 2783 (93.4%) |

Cox Regression Model for Time to First Positively Adjudicated Primary Endpoint Including Treatment Group. Delay between randomization and index MI and Delay between randomization and index MI × Randomized treatment group interaction.

| Interaction Effect | P-value |
|---|---|
| Delay between randomization and index MI × Randomized intermittent group | 0.5867 |

| Delay between randomization and index MI | Effect | HR (95% CI) | P-value |
|---|---|---|---|
| [0-5] days | Colchicine vs. placebo | 0.67 (0.45; 1.01) | 0.0545 |
| [6-30] days | Colchicine vs. placebo | 0.78 (0.59; 1.03) | 00.764 |

Notes: Model based on N = 4661 observations.
Deaths of undetermined cause were classified as CV deaths.

TABLE 7

Effect of Colchicine with TTI of < 5 days calculated adjusted basic model

| DELAY BETWEEN RANDOMIZATION AND INDEX MI | POSITIVELY ADJUDICATED PRIMARY ENDPOINT | Placebo N = 2339 | Colchicine N = 2322 | All N = 4661 |
|---|---|---|---|---|
| [0-5] days | N | 821 | 859 | 1680 |
| | Yes | 56 (6.8%) | 40 (4.7%) | 96 (5.7%) |
| | No | 765 (93.2%) | 819 (95.3%) | 1584 (94.3%) |
| [6-30] days | n | 1518 | 1463 | 2981 |
| | Yes | 113 (7.4%) | 85 (5.8%) | 198 (6.6%) |
| | No | 1405 (92.6%) | 1378 (94.2%) | 2783 (93.4%) |

Cox Regression Model for Time to First Positively Adjudicated Primary Endpoint Including Treatment Group. Delay between randomization and index MI and Delay between randomization and index MI × Randomized treatment group interaction. Age at randomization (years). History of diabetes, Prior coronary revascularization (prior PCI or prior CABG) and Prior Heart Failure

| Interaction Effect | P-value |
|---|---|
| Delay between randomization and index MI × Randomized intermittent group | 0.5515 |

| Delay between randomization and index MI | Effect | HR (95% CI) | P-value |
|---|---|---|---|
| [0-5] days | Colchicine vs. placebo | 4.43 (0.45, 1.02) | 0.0631 |
| [6-30] days | Colchicine vs. placebo | 0.35 (0.60, 1.05) | 0.1023 |

Notes: Model based on N = 4661 observations.
Deaths of undetermined cause were classified as CV deaths For a TTI of 5 days or less, colchicine showed borderline significance with respect to the benefits of administering colchicine within 5 days of an MI. This data suggests that some benefit is still possible administering colchicine 5 days after an MI, having HR 0.68 (0.45-1.02) and p=0.063 using the adjusted model.

Effects of Time-to-Treatment Initiation on the Secondary and Exploratory Efficacy Endpoints The effects of colchicine on the secondary and exploratory endpoints are shown in Table 3. The secondary efficacy endpoint consisting of a composite of CV death, cardiac arrest, myocardial infarction or stroke occurred in 3.3% of the patients in the colchicine group and in 6.1% of those in the placebo group when TTI was between days 0 and 3 (HR=0.55; 95% CI, 0.32-0.95, FIG. 3). The exploratory endpoint of all coronary revascularizations, not coronary revascularizations limited to those observed as the primary composite endpoint, including urgent revascularization following unstable angina and hospitalization, occurred in 5.5% of patients in the colchicine group, as compared to 8.7% of those in the placebo group when TTI was between days 0 and 3 (HR=0.63, 95% CI 0.40-0.97). There were 6 deaths in both study groups when TTI was between days 0 and 3 (HR=1.03, 95% 0.33-3.19).

This TTI analysis of COLCOT shows that early initiation of low-dose colchicine within the first 3 days after MI is associated with a reduction of 48% in the risk of the primary endpoint consisting of a composite of CV death, resuscitated cardiac arrest, MI, stroke, or urgent hospitalization for angina requiring coronary revascularization, in comparison with placebo. This result was due to a lower incidence of MIs, strokes and urgent hospitalizations for angina leading to coronary revascularization. The secondary efficacy endpoint consisting of a composite of CV death, resuscitated cardiac arrest, MI or stroke was also significantly reduced by 45% with early initiation of low-dose colchicine. The benefits were more marked when treatment was initiated within the first 3 days after MI, as compared to between days 4 and 30, supporting the strategy of in-hospital initiation of colchicine in order to improve CV outcomes post-MI.

The main COLCOT results revealed that colchicine reduced the risk of ischemic CV events by 23% in the post-MI setting. Results from the present COLCOT analysis suggest that early suppression of inflammation after MI provides even greater benefits, with a reduction of 48% in the risk of the composite primary endpoint when colchicine was initiated between days 0 and 3. The demonstrated cost-effectiveness of low-dose colchicine also supports its large-scale use after MI. Results of the LoDoCo2 study of patients with stable coronary artery disease complement and further support those of COLCOT in the post-MI setting (see Nidorf at al. *N Engl Med,* 2020. and Tong et al. *Circulation,* 2020).

Early initiation of low-dose colchicine after MI greatly reduced the risk of ischemic CV events compared with placebo. These results support in-hospital initiation of adjunctive anti-inflammatory therapy with colchicine for post-MI prevention.

Statistical Analysis

For the COLCOT trial, it was estimated that a sample of approximately 4500 patients undergoing randomization (with 2250 patients in each group) or, in terms of events, a total number of 301 patients with a first positively adjudicated primary end-point event would yield adequate power. The sample-size calculation was based on the primary efficacy end point and assumed a 27% lower risk with colchicine than with placebo, indicated by a hazard ratio of 0.724. With the use of a two-sided test at the 0.05 significance level, the trial would have 80% power if it continued until 301 positively adjudicated primary events occurred in the combined trial groups. The trial design assumed an event rate of 7% in the placebo group at 24 months, an 18-month recruitment period during which patients would be uniformly recruited, a 24-month minimum follow-up period, and a 1% annual rate of loss to follow-up or withdrawal of consent.

The efficacy analyses were conducted with the use of positively adjudicated data and according to the intention-to-treat principle. The primary end point was compared between the two trial groups with the use of a log-rank test, and the hazard ratio from a Cox proportional-hazards model, with a 95% confidence interval, was calculated. A Cox proportional-hazards model with adjustment for important baseline characteristics was also used as prespecified in the protocol.

Figure 2:
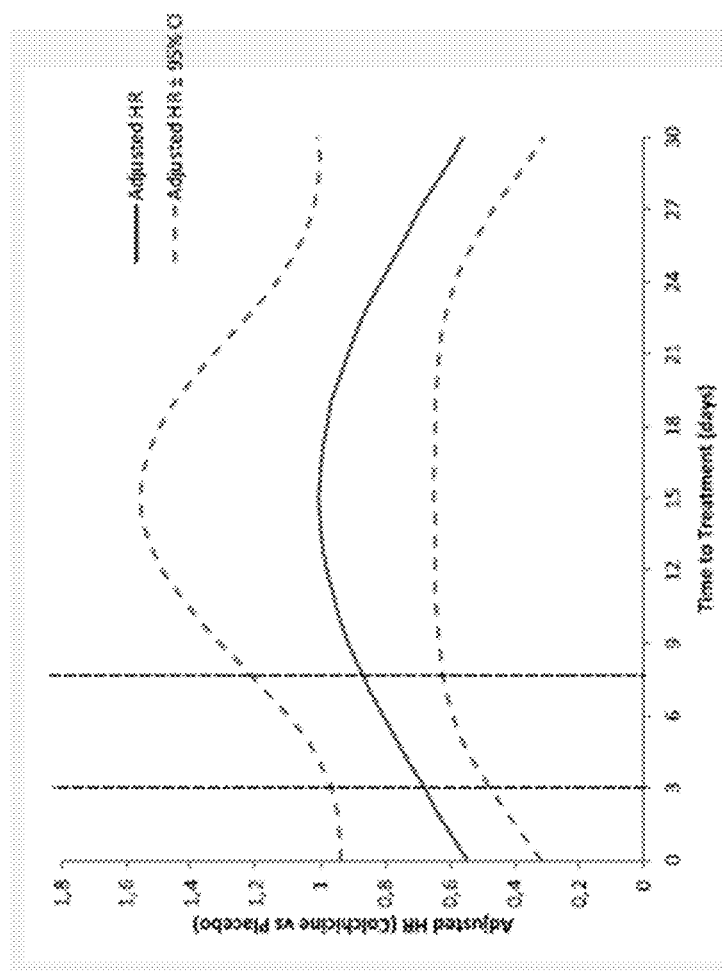
FIG. 2 is a graph of the association between the time-to-treatment initiation and the adjusted hazard ratio (solid line) with the 95% confidence intervals of the adjusted hazard ratio (dashed line) calculated using a quadratic multivariable Cox regression model.
Figure 3A:
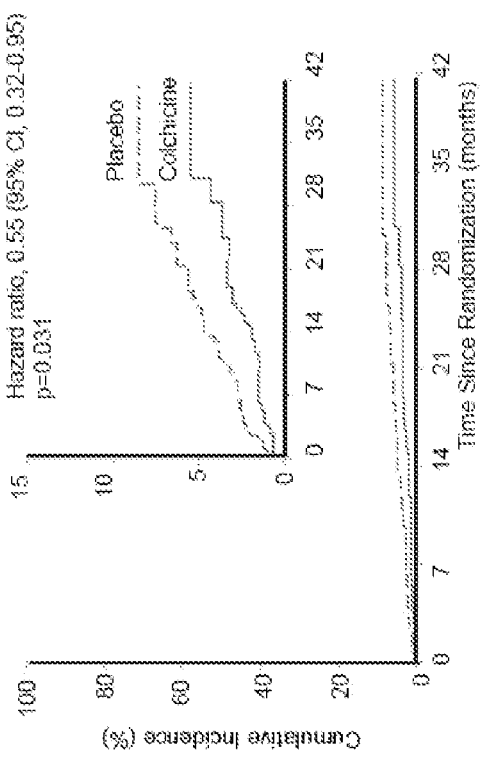
FIG. 3A is a graph of the cumulative incidence of cardiovascular events (time-to-treatment population). Shown are the Kaplan-Meier event curves for the primary efficacy composite end point (a composite of cardiovascular death, resuscitated cardiac arrest, MI, stroke, or urgent hospitalization for angina requiring coronary revascularization) in the colchicine group and the placebo group for patients with a time-to-treatment initiation of ≤3 days. The inset shows the same data on an enlarged y-axis.

For the present TTI analysis, the data were centrally analyzed by an independent academic biostatistics center at the Montreal Health Innovations Coordinating Center. The analysis was conducted amongst patients who received at least one dose of the study medication (referred to as the safety population in the main protocol, FIG. 1). TTI was defined as the length of time in days between the index MI and the initiation of the study medication, and three specific cutoffs were analyzed (5 day 3, days 4 to 7, and 2 day 8). Early initiation of therapy was defined as TTI≤3 days. Baseline characteristics were summarized using counts and percentages for categorical variables and mean±standard deviation (SD) for continuous variables. For each baseline characteristic, comparisons were made using ANOVA for continuous variables and Chi-Square test for categorical variables according to TTI strata. Analyses of the efficacy endpoints, expressed as time to event, were conducted according to time to treatment initiation. Adjusted hazard ratios (HR) along with 95% confidence intervals (CI) were calculated from stepwise multivariable Cox regression models adjusted for the same covariates that were used in the main analysis of the COLCOT trial (FIG. 2). All statistical tests were two-sided and conducted at the 0.05 significance level. Statistical analyses were performed with the use of SAS software, version 9.4 (SAS Institute).

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1: Meta-Analysis of Randomized Controlled Trials (RCTs) of Colchicine for Secondary Prevention of Cardiovascular Disease Data Sources Medline (PUBMED), EMBASE, and Cochrane central were searched to identify RCTs comparing colchicine to placebo or no colchicine for secondary cardiovascular prevention (inception to Sep. 1, 2020). To maximized sensitivity, citation chasing was performed in Google Scholar, Scopus, and Web of Science. Secondary prevention was defined as patients with clinically manifest or established CAD. Query terms included "colchicine", "coronary artery disease", "acute coronary syndrome", "myocardial infarction", "cardiovascular disease", "atherosclerosis", and "secondary prevention", either separately or in combination.

Study Selection, Data Extraction, and Bias Assessment

RCTs that met the following criteria were included in the meta-analysis: 1) compared daily use of low-dose (0.5 mg) colchicine to placebo or no colchicine for secondary cardiovascular prevention; 2) the study reported at least one of the following outcomes: cardiovascular death, MI, stroke, cardiac arrest, or urgent coronary revascularization; 3) other than the trial medication, patients in both arms were treated in accordance to guideline directed medical therapy; 4) the minimum follow-up was at least 1 year; and 5) trials were published in a peer-reviewed scientific journal. Review articles, editorials, meta-analyses, observational studies, and published abstracts were excluded from the present meta-analysis.

Study selection was performed by two independent reviewers, using two levels of screening. At the first level, titles and abstracts of searched studies were screened, followed by review of full texts. The reviewers were not blinded to the title of the journals, authors, or affiliated institutions. Reasons for exclusion were recorded and any discrepancies were discussed until a consensus was achieved.

Using standardized forms, data on study characteristics, patient characteristics, and outcomes were extracted on the intent-to-treat population independently by two reviewers from each eligible study. The Cochrane Collaboration risk-of-bias tool for randomized trials was used to evaluate study quality. The meta-analysis was conducted in accordance to the Preferred Reporting Items for Systematic Reviews and Meta-Analyses (PRISMA) guidelines.

Outcomes

The primary efficacy endpoint was a composite of cardiovascular death, MI, ischemic stroke, and urgent coronary revascularization. Secondary efficacy endpoints consisted of the components of the primary endpoint, composite of cardiovascular death, MI, and ischemic stroke, as well as deep vein thrombosis or pulmonary embolus, and atrial fibrillation (AF). To maximize consistency in pooling efficacy endpoints among trials, the primary and secondary composite efficacy and stroke endpoints in COLCOT were modified to meet the definition of primary and stroke endpoints of the LoDoCo2 trial. Therefore, adjudicated events of resuscitated cardiac arrest and non-ischemic stroke in COLCOT were excluded from the pooled primary endpoint. The component endpoint of stroke was also restricted to include only ischemic strokes. Incidence rates and hazards ratios (HRs) were calculated for the new primary composite endpoint and ischemic stroke endpoint using individual patient data from COLCOT.

Safety outcomes were limited to serious adverse events (SAEs) and included all-cause and non-cardiovascular mortality, hospitalization for gastrointestinal event, infection, and pneumonia, as well as diagnosis of cancer. Incidence of SAEs were recalculated for COLCOT using the intent-to-treat population.

Data Synthesis and Statistical Analyses

The DerSimonian and Laird random-effects model was used to calculate the pooled HR and corresponding 95% confidence intervals (CI) for primary and secondary endpoints in the overall trial and in subgroup analyses of the primary endpoint. For safety outcomes, the DerSimonian and Laird random-effects model was used to compute risk ratios (RR) and corresponding 95% CIs. Heterogeneity was evaluated with the Higgins $I^2$ statistic. $I^2$ values of <25%, 25-75%, and >75% were considered to indicate low, moderate, and high degrees of heterogeneity, respectively. In subgroup analyses, the $Q_b$ statistic was calculated to determine inconsistency and variability in the treatment effect between strata. Publication and small study bias were assessed with the Egger's regression test and visually by asymmetry in funnel plots. Sensitivity analyses were performed for the primary composite and component outcomes for 1) RCTs in patients with acute coronary syndrome (COLCOT and COPS), and 2) RCTs in patients with stable CAD (LoDoCo and LoDoCo2); and after exclusion of 3) the LoDoCo trial [open-label trial and control group was not randomized to placebo] and 4) the LoDoCo and COPS [increased dose (0.5 mg twice daily) of colchicine prescribed during first month] trials. Statistical analyses were performed using SAS software version 9.4 (SAS Institute, Cary, N.C.) and Stata (Version 16, StataCorp, College Station, Tex.).

Results

Literature Search Results and Risk of Bias

The search strategy identified 79 studies. After the first- and second-level screening processes, four RCTs were retained in the present meta-analysis. The characteristics of included RCTs are listed in Table 8. The Low-Dose Colchicine (LoDoCo) and Low-Dose Colchicine 2 (LoDoCo2) trials assessed the efficacy of colchicine in patients with stable CAD (defined as clinically stable for ≥6 months) (see, Nidorf et al. *N Engl Med*, 2020. and Tong et al. *Circulation*, 2020). In comparison, the Colchicine Cardiovascular Outcomes Trial (COLCOT) was conducted in patients who had a recent MI (≤30 days) and the Colchicine in Patients with acute coronary Syndrome (COPS) trial enrolled patients with acute coronary syndromes (ACS) (see, Tardif et al. *N Engl J Med*.)

The pooled sample size of enrolled patients was 11,594, of which 5774 patients were randomized to colchicine and 5820 patients were randomized to placebo (or no colchicine, in the LoDoCo trial only). Three trials were designated as "low risk" for overall bias (see, Tardif et al. *N Engl J Med.*, Nidorf et al., *N Engl J Med*, 2020, and Tong et al, *Circulation*, 2020) and 1 trial was marked as being of "some concern" (see, Nirdorf et al., *J Am Coll Cardiol*. 2013; 61: 404-10) in the Cochrane Collaboration risk-of-bias assessment.

TABLE 8

| | Study characteristics | | | |
| --- | --- | --- | --- | --- |
| | LoDoCo | COLCOT | COPS | LoDoCo2 |
| Year | 2013 | 2019 | 2020 | 2020 |
| Study design | Single-blind RCT | Double-blind, placebo controlled RCT | Double-blind, placebo controlled RCT | Double-blind, placebo controlled RCT |
| Study population | Stable CAD | Recent MI (<30 days) | ACS | Stable CAD |

TABLE 8-continued

| | Study characteristics | | | |
|---|---|---|---|---|
| | LoDoCo | COLCOT | COPS | LoDoCo2 |
| N | 532 | 4,745 | 795 | 5,522 |
| Key inclusion criteria | Angiographically proven CAD; clinically stable for <= 6 months | MI within 30 days prior; completed planned percutaneous revascularization procedures; treated according to national guidelines that included intensive use of statins | ACS (STEMI/NSTEMI/UA); Evidenced CAD on coronary angiography, managed with either PCI or medical therapy | Evidence of CAD on invasive angiography or computed tomography angiography or a coronary calcium score of ≥ 400 Agaston units on a coronary-artery calcium scan; clinically stable condition for ≥ 6 months |
| Key exclusion criteria | Bypass surgery within 10 years prior | Severe heart failure; left ventricular ejection fraction < 35%; stroke within the previous 3 months; type 2 index MI; coronary-bypass surgery either within previous 3 years or planned; severe renal or hepatic disease; known cancer | CAD requiring surgical revascularization pre-existing long-term colchicine use or immunosuppressant therapy; severe hepatic or renal insufficiency; known active malignancy | Moderate-to-severe renal impairment; severe heart failure; severe valvular disease |
| Median follow-up | 24 months | 22.6 months | 12 months | 28.6 months |
| Primary endpoint | Composite: ACS, out-of-hospital cardiac arrest, or non-cardioembolic ischemic stroke | Composite: CV mortality, resuscitated cardiac arrest, MI, stroke, or urgent hospitalization for angina requiring revascularization | Composite: All-cause mortality, ACS (STEMI/NSTEMI/UA), ischemia-driven revascularization, or non-cardioembolic ischemic stroke | Composite: CV death, MI, ischemic stroke, or ischemia-driven coronary revascularization |

*ACS, acute coronary syndrome; CAD, coronary artery disease; CV, cardiovascular; MI, myocardial infarction; RCT, randomized controlled trial; STEM, ST elevation myocardial infarction; NSTEMI, non-ST elevation myocardial infarction; UA, unstable angina Patient Characteristics Baseline patient characteristics for each RCT are summarized in Table 9. The mean age of patients ranged from 60 to 67 years. In all trials, <20% of enrolled patients were women and more than 90% of patients were on concomitant statin therapy. LoDoCo and LoDoCo2 trials had a higher proportion of patients who underwent prior coronary revascularization [percutaneous coronary intervention (PCI) and coronary artery bypass graft (CABG) surgery]. The distribution of all other patient characteristics was relatively similar between trials.

TABLE 9

| | Patient characteristics at baseline | | | | | | | |
|---|---|---|---|---|---|---|---|---|
| | LoDoCo | | COLCOT | | COPS | | LoDoCo2 | |
| | Colchicine N = 250 | Control N = 282 | Colchicine N = 2366 | Placebo N = 2379 | Colchicine N = 396 | Placebo N = 399 | Colchicine N = 2762 | Placebo N = 2760 |
| Age, years (mean ± SD) | 67 ± 9.2 | 66 ± 9.6 | 60.6 ± 10.7 | 60.5 ± 10.6 | 59.7 ± 10.2 | 60.0 ± 10.4 | 65.8 ± 8.4 | 65.9 ± 8.7 |
| Women (%) | 11.2% | 11.0% | 19.9% | 18.4% | 18.7% | 22.3% | 16.5% | 14.1% |
| Hypertension (%) | Not reported | Not reported | 50.1% | 52.0% | 50.8% | 49.9% | 51.4% | 50.3% |
| Diabetes (%) | 27.6% | 32.6% | 19.5% | 20.9% | 18.9% | 19.0% | 17.8% | 18.7% |

TABLE 9-continued

| Patient characteristics at baseline | | | | | | | | |
|---|---|---|---|---|---|---|---|---|
| | LoDoCo | | COLCOT | | COPS | | LoDoCo2 | |
| | Colchicine N = 250 | Control N = 282 | Colchicine N = 2366 | Placebo N = 2379 | Colchicine N = 396 | Placebo N = 399 | Colchicine N = 2762 | Placebo N = 2760 |
| History of PCI (%) | 55.2% | 59.9% | 16.6% | 17.1% | 12.9% | 12.5% | 76.0% | 75.3% |
| History of CABG (%) | 15.6% | 22.0% | 2.9% | 3.4% | 3.8% | 4.8% | 11.5% | 14.2% |
| Statin use (%) | 94.0%* | 96.1%* | 98.9% | 99.1% | 98.2% | 99.5% | 93.9% | 94.0% |

*The LoDoCo trial only reported use of high dose statins, not any statin use.

Clinical Efficacy Endpoints

Clinical efficacy results from each trial are presented in Table 10. In patients with CAD, the addition of colchicine to standard medical therapy was associated with a statistically significant reduction in the primary composite endpoint of cardiovascular mortality, MI, ischemic stroke, and urgent coronary revascularization, compared to patients on placebo or no colchicine [pooled HR 0.68 (95% CI 0.54-0.81); $I^2$=37.7%]. The reduction in cardiovascular events in patients randomized to colchicine was driven by statistically significant reductions in the incidence of MIs [pooled HR 0.62 (95% CI 0.3-0.88); $I^2$=68.76%], ischemic strokes [pooled HR 0.38 (95% CI 0.13-0.63); $I^2$=0.0%], and urgent coronary revascularization [pooled HR 0.58 (95% CI 0.30-0.82); $I^2$=65.1%]. However, there was no statistically significant difference detected for cardiovascular mortality. Sensitivity analyses that pooled the results of COLCOT and LoDoCo2 trials demonstrated similar effect estimates for the primary composite and component outcomes, although magnitude of effect and heterogeneity ($I^2$) between studies decreased.

TABLE 10

| Study efficacy outcomes | | | | | | | | |
|---|---|---|---|---|---|---|---|---|
| | LoDoCo[11] | | COLCOT[10] | | COPS[13] | | LoDoCo2[12] | |
| | Colchicine N = 250 | Control N = 282 | Colchicine N = 2366 | Placebo N = 2379 | Colchicine N = 396 | Placebo N = 399 | Colchicine N = 2762 | Placebo N = 2760 |
| Primary composite outcome: Cardiovascular mortality, myocardial infarction, ischemic stroke, urgent revascularization | | | | | | | | |
| Events, N (%) | NA | NA | 130 (5.5%) | 168 (7.1%) | 19 (4.8%) | 41 (10.3%) | 187 (6.8%) | 264 (9.6%) |
| HR (95% CI) | NA | | 0.77 (0.61-0.97) | | 0.47 (0.27-0.82) | | 0.69 (0.57-0.83) | |
| Cardiovascular mortality | | | | | | | | |
| Events, N (%) | NA | NA | 20 (0.8%) | 24 (1.0%) | 3 (0.8%) | 1 (0.3%) | 20 (0.7%) | 25 (0.9%) |
| HR (95% CI) | NA | | 0.84 (0.46-1.52) | | 3.09 (0.32-29.71) | | 0.80 (0.44-1.44) | |
| Myocardial infarction | | | | | | | | |
| Events, N (%) | 4 (1.6%) | 14 (5.6%) | 89 (3.8%) | 98 (4.1%) | 11 (3.7%) | 22 (5.5%) | 83 (3.0%) | 116 (4.2%) |
| HR (95% CI) | 0.25 (0.08-0.76) | | 0.91 (0.68-1.21) | | 0.52 (0.25-1.07) | | 0.70 (0.53-0.93) | |
| Ischemic stroke | | | | | | | | |
| Events, N (%) | 1 (0.4%) | 4 (1.6%) | 4 (0.2%) | 16 (0.7%) | 2 (0.5%) | 6 (1.5%) | 16 (0.6%) | 24 (0.9%) |
| HR (95% CI) | 0.23 (0.03-2.03) | | 0.25 (0.08-0.75) | | 0.34 (0.07-1.70) | | 0.66 (0.35-1.25) | |
| Urgent coronary revascularization | | | | | | | | |
| Events, N (%) | NA | NA | 25 (1.1%) | 50 (2.1%) | 3 (0.8%) | 12 (3.0%) | 135 (4.9%) | 177 (6.4%) |
| HR (95% CI) | NA | | 0.50 (0.31-0.81) | | 0.26 (0.07-0.92) | | 0.75 (0.60-0.94) | |

*NA = not applicable. A study result was designed NA when the outcome in the study did not closely match the outcome in the present meta-analysis.

In sensitivity analyses of ACS trials (COLCOT and COPS; N=5540), the primary composite endpoint, MI, and urgent coronary revascularizations were statistically significantly reduced in patients randomized to colchicine compared to placebo. Among patients with stable CAD (LoDoCo and LoDoCo 2; N=6054), the only comparable outcome between trials was MI which was statistically significantly decreased with colchicine compared to placebo.

Although there was no statistically significant difference in the incidence of key secondary endpoints, there was a trend towards reduced AF diagnoses and AF episodes among patients randomized to colchicine [pooled HR 0.86 (95% CI 0.67-1.04); $I^2$=0.0%].

Visual inspection of funnel plots and the results of the Eggers test indicated there was no significant risk of publication bias for all outcomes (p>0.05 for all) except urgent coronary revascularization (p=0.02).

Subgroup Analyses

The statistically significant reduction in the incidence of the primary composite cardiovascular endpoint among patients randomized to colchicine was consistent for most subgroup analyses. There was no significant heterogeneity of the effect of colchicine in the different subgroups studied. Overall, the $Q_b$ statistic suggests that there is minimal variability and inconsistency in the treatment effect between strata in subgroup analyses (p>0.05 for all).

Major Adverse Events

Figure 3B:
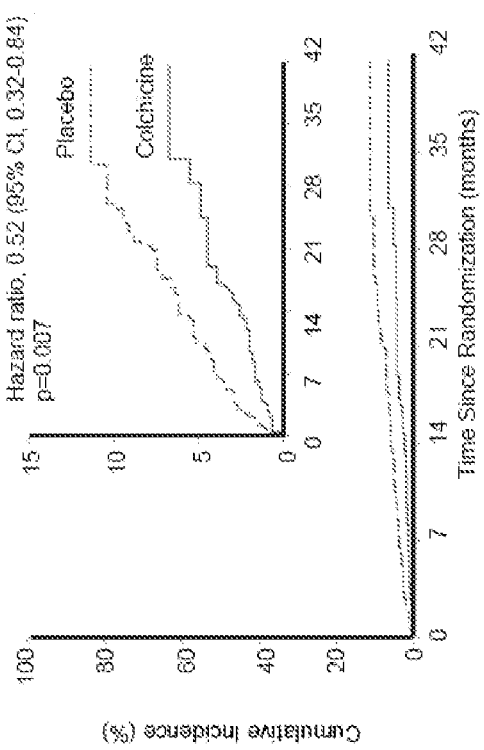
FIG. 3B is a graph of the cumulative incidence of cardiovascular events (time-to-treatment population). Shown are the Kaplan-Meier event curves for the secondary efficacy composite end point (a composite of cardiovascular death, resuscitated cardiac arrest, myocardial infarction, or stroke) in the colchicine group and the placebo group for patients with a time-to-treatment initiation of ≤3 days. The inset shows the same data on an enlarged y-axis.

There was no statistically significant difference between treatment arms for the risk of all-cause [pooled RR 1.04 (95% CI 0.61-1.78); $I^2$=62.01%] and non-cardiovascular mortality [pooled RR 1.38 (95% CI 0.99-1.93); $I^2$=0.0%] (FIG. 3). The rates of infections, pneumonias, hospitalizations for gastrointestinal events, and diagnoses of cancer were also not significantly different. For pneumonia, there was a high degree of heterogeneity between trials with opposite directions for the treatment effect ($I^2$=81.5%).

In this contemporary meta-analysis of RCTs comparing colchicine to placebo (or no colchicine) for secondary cardiovascular prevention, we found that: 1) treatment with colchicine was associated with a 32% reduction in the incidence of major cardiovascular events; 2) significantly fewer MIs, ischemic strokes, and urgent coronary revascularizations were the primary drivers for the overall decrease in cardiovascular events; 3) the protective treatment effect of colchicine was relatively consistent among most subgroups studied, and 4) colchicine had a favorable safety profile. This is the first comprehensive meta-analysis of RCTs evaluating efficacy and safety of colchicine for secondary cardiovascular prevention in which the endpoints were harmonized across trials. Overall, the synthesis of current evidence in the present meta-analysis indicates that treatment with colchicine for secondary cardiovascular prevention confers beneficial clinical effects.

Secondary Prevention of Cardiovascular Diseases

Although the 4 RCTs investigated the efficacy of colchicine in different segments of the CAD population, including stable CAD, recent MI, and ACS, the results of all trials consistently demonstrated that colchicine was protective against a composite endpoint of cardiovascular mortality, MI, ischemic stroke, and urgent coronary revascularization. The individual trials were not powered to detect statistically significant differences in the components of the primary endpoint. Whereas all trials showed a decrease in urgent coronary revascularizations among patients randomized to colchicine, only COLCOT detected a reduction in ischemic strokes [HR 0.25 (95% CI 0.08-0.75)] and LoDoCo2 a decrease in MIs [HR 0.70 (95% CI 0.53-0.93)]. Pooling HRs from the RCTs revealed that the attenuated risk of major cardiovascular events was attributed to risk reductions of 38%, 62%, and 44% for MIs, ischemic strokes, and urgent coronary revascularization, respectively. Although the 2 largest trials, COLCOT and LoDoCo2, contributed the most weight to analyses, the inclusion of LoDoCo and COPS tended to increase the magnitude of the risk reduction by 4-5%.

Individual trials and pooled results suggest that there is no difference in the incidence of cardiovascular or all-cause mortality with colchicine. These pooled analyses provide reassurance about the safety of colchicine for the outcome of all-cause mortality. Results from both the LoDoCo2 and COPs trials showed a trend towards increased all-cause mortality with colchicine, although neither reached statistical significance [LoDoCo2 HR 1.21 (95% CI 0.86-1.71) and COPS HR 8.20 (95% 1.02-65.61)]. The increased power from pooled analyses demonstrated that the effect of colchicine on all-cause mortality was closer to null or no effect than suggested by individual trials [pooled RR 1.04 (95% CI 0.61-1.78)].

The anti-inflammatory properties of colchicine work through various mechanisms to inhibit the pathogenesis of CAD, and subsequently reduce the incidence of ischemic cardiovascular events. In addition to targeting the NLRP3 inflammasome leading to the reduction of circulating levels of IL-1β and IL-6, colchicine also inhibits cholesterol crystals that promote inflammation and plaque instability in atherosclerosis.

Treatment Effects Across Subgroups

The treatment effect of colchicine was similar with overlapping confidence intervals across age categories (≤65 or >65 years), presence or absence of diabetes and hypertension, and among patients with or without prior coronary revascularization. Although the risk reduction appeared less marked in women compared to men, less than 20% of trial populations were women (1977 women compared to 9617 men). It is, therefore, possible that the lack of a statistically significant reduction in cardiovascular events with colchicine in the subgroup analysis of women reflects limited power. There was no significant heterogeneity between the effects in subgroups and that in the overall population.

Safety

Colchicine has an established safety profile from its centuries of use to treat gout. There was a numerical imbalance in the number of non-cardiovascular deaths between study arms, which did not reach statistical significance. Importantly, there was no effect of colchicine on all-cause mortality. In the COPS study, the increased dose of colchicine during the first month of follow-up might have contributed to higher non-cardiovascular deaths. In addition, 3 of 5 colchicine patients who died from non-cardiovascular causes in COPS had also discontinued colchicine prior to date of death, which may suggest that on-treatment analyses may provide further evidence to the safety of colchicine for non-cardiovascular mortality. Furthermore, the quality of follow-up in COPS was poor, with more than twice the number of patients with incomplete vital status than that of deaths due to inadequate resources (2 part-time healthcare workers following 795 patients). In contrast, the quality of follow-up and rate of vital status ascertainment of the 10,267 patients included in COLCOT and LoDoCo2 were excellent and did not reveal a significant difference in non-cardiovascular mortality between study arms. Finally, the meta-analysis showed no difference in all-cause mortality between groups.

Only the COLCOT trial detected a difference in the rate of pneumonia between patients randomized to colchicine (0.9%) or placebo (0.4%). Pooled analyses of COLCOT and LoDoCo2 did not show an increased risk of pneumonia with colchicine, suggesting this result in the former may have been due to chance. The lack of a difference between groups for infections, hospitalizations, and diagnoses of cancer further validates that colchicine is safe to use in patients with CAD.

As we did not have access to patient-level data from 3 of 4 trials, only modified study-level data was used for the present meta-analysis. Although meta-analyses based on aggregate patient data continue to be the mainstay of systematic reviews that inform clinical practice, meta-analyses based on individual patient data have several advantages including the ability to verify data, address new questions, and adjust for the same variables across studies. Finally, the small number of eligible studies precluded meta-regression analyses to determine the influence of specific variables or effect modifiers on the association between colchicine and cardiovascular events. Nevertheless, the potential for effect modification was addressed in part by subgroup analyses.

In patients with CAD, the addition of low-dose colchicine to standard medical therapy consistently and significantly reduces the incidence of major cardiovascular events compared to standard medical therapy alone. With the exception of cardiovascular mortality, significant reductions were observed for components of the primary outcome, including MIs, ischemic strokes, and urgent coronary revascularizations.

Example 2: Administration of Low-Dose Colchicine after Myocardial Infarction

The results of the main COLCOT trial support that the use of colchicine in patients who have had a myocardial infarction in the past 30 days significantly improved their quality of life in several ways. The COLCOT trial was performed as follows. A randomized, double-blind trial involving patients recruited within 30 days after a myocardial infarction was performed. The patients were randomly assigned to receive either low-dose colchicine (0.5 mg once daily) or placebo. A total of 4745 patients were enrolled; 2386 patients were assigned to the colchicine group, and 2379 to the placebo group. Patients were followed for a median of 22.6 months to observe the occurrence of the primary efficacy end point which was a composite of death from cardiovascular causes, resuscitated cardiac arrest, myocardial infarction, stroke, or urgent hospitalization for angina leading to coronary revascularization. The components of the primary end point and safety were also assessed in this study.

In this randomized, double-blind, placebo-controlled, investigator-initiated trial, we assigned patients in a 1:1 ratio to receive either colchicine (at a dose of 0.5 mg once daily) or placebo. The trial protocol, available at NEJM.org, was designed by a trial steering committee.

Trial Population

Adult patients were eligible if they had had a myocardial infarction within 30 days before enrollment, had completed any planned percutaneous revascularization procedures, and were treated according to national guidelines that included the intensive use of statins.

Patients were excluded if they had severe heart failure, a left ventricular ejection fraction of less than 35%, stroke within the previous 3 months, a type 2 index myocardial infarction, coronary-bypass surgery either within the previous 3 years or planned, a history of noncutaneous cancer within the previous 3 years, inflammatory bowel disease or chronic diarrhea, neuromuscular disease or a nontransient creatine kinase level that was greater than three times the upper limit of the normal range (unless due to infarction), clinically significant nontransient hematologic abnormalities, severe renal disease with a serum creatinine level that was greater than two times the upper limit of the normal range; severe hepatic disease, drug or alcohol abuse, current or planned long-term systemic glucocorticoid therapy, or a history of clinically significant sensitivity to colchicine.

Witten informed consent was obtained from all the patients before enrollment. Clinical evaluations occurred at 1 month and 3 months after randomization and every 3 months thereafter.

End Points

The primary efficacy end point was a composite of death from cardiovascular causes, resuscitated cardiac arrest, myocardial infarction, stroke, or urgent hospitalization for angina leading to coronary revascularization in a time-to-event analysis.

The secondary end points consisted of the components of the primary efficacy end point; a composite of death from cardiovascular causes, resuscitated cardiac arrest, myocardial infarction, or stroke; and total mortality in time-to-event analyses. Coronary revascularization, hospitalization for heart failure, atrial fibrillation, and deep venous thrombosis or pulmonary embolus were prespecified as exploratory end points in the protocol.

Additional prespecified exploratory end points included the change from baseline to 6 months in the high-sensitivity C-reactive protein level and the change from baseline to 12 months in the white-cell count. The C-reactive protein biomarker substudy was implemented after a protocol amendment and was optional for sites and for patients; 34 sites chose to participate in this substudy.

All serious adverse events were recorded. The only other adverse events recorded were those that were considered to be related to the gastrointestinal system, events that were judged by the investigator to be related to colchicine or placebo, or laboratory abnormalities that had been judged by the investigator to be clinically significant.

Statistical Analysis

In this event-driven trial, it was estimated that a sample of approximately 4500 patients undergoing randomization (with 2250 patients in each group) or, in terms of events, a total number of 301 patients with a first positively adjudicated primary end-point event would yield adequate power. The sample-size calculation was based on the primary efficacy end point and assumed a 27% lower risk with colchicine than with placebo, indicated by a hazard ratio of 0.724. With the use of a two-sided test at the 0.05 significance level, the trial would have 80% power if it continued until 301 positively adjudicated primary events occurred in the combined trial groups. The trial design assumed an event rate of 7% in the placebo group at 24 months, an 18-month recruitment period during which patients would be uniformly recruited, a 24-month minimum follow-up period, and a 1% annual rate of loss to follow-up or withdrawal of consent.

The efficacy analyses were conducted with the use of positively adjudicated data and according to the intention-to-treat principle. The primary end point was compared between the two trial groups with the use of a log-rank test, and the hazard ratio from a Cox proportional-hazards model, with a 95% confidence interval, was calculated. A Cox proportional-hazards model with adjustment for important baseline characteristics was also used as prespecified in the protocol.

The analysis of the primary end point was repeated in the per-protocol population (i.e., patients without major protocol deviations). Secondary and exploratory end points expressed as time to event were analyzed similarly. The changes from baseline to follow-up were analyzed with the use of an analysis of covariance model with adjustment for baseline value, and estimates of treatment effect are presented with 95% confidence intervals.

The efficacy end points expressed as time to event could be assessed in all patients because the event dates and censoring dates were complete, with the exception of one incomplete event date for atrial fibrillation; therefore, imputation for missing data was not done.

In the analysis of time to event, the following censoring rules were used. For death from any cause and death from cardiovascular causes, data from event-free patients who completed the trial were censored at the date of trial completion, and data from patients who did not complete the trial, such as those who were lost to follow-up or who withdrew consent, were censored at the date of last contact or the date of the assessment of survival status, whichever was later.

For the analysis of death from cardiovascular causes, patients who died from a noncardiovascular cause had their data censored at the time of death.

For all other end points, including the primary end point, the same censoring rules applied, but the survival status was not used because no formal assessment of end points was done at the assessment of survival status.

An analysis of the components of the primary end point with death from noncardiovascular causes as a competing event for death from cardiovascular causes, and with death from any cause as a competing event for the other components, was conducted with the use of the Fine and Gray subdistribution hazard model (Fine J P and Gray R J, A proportional hazards model for the subdistribution of a competing risk. *J Am Stat Assoc* 1999; 94:496-509). No missing data were imputed except for age To account for the occurrence of multiple primary end-point events within patients, recurrent-event analyses were undertaken with the use of negative binomial regression, Andersen-Gill, and Wei-n-Weissfeld models (Rogers J K et al., Analysing recurrent hospitalizations in heart failure: a review of statistical methodology, with application to CHARM-Preserved. *Eur J Heart Fail* 2014; 16:33-40; Andersen P K and GIN R D, Cox's regression model for counting processes: a large sample study. *Ann Stat* 1982; 10:1100-20; Lin D Y and Wei L J, The robust inference for the proportional hazards model. *J Am Stat Assoc* 1989; 84:1074-8; Lin D Y et al. Semiparametric regression for the mean and rate functions of recurrent events. *J R Stat Soc* 2000; 62:711-30; Wei L J and Glidden D V, An overview of statistical methods for multiple failure time data in clinical trials. *Stat Med* 1997; 16:833-9; Ghosh D, Methods for analysis of multiple events in the presence of death. *Control Clin Trials* 2000; 21:115-26; Li Q H and Lagakos S W, Use of the Wei-Lin-Weissfeld method for the analysis of a recurring and a terminating event. *Stat Med* 1997; 16:925-40; Metcalfe C and Thompson S G, The importance of varying the event generation process in simulation studies of statistical methods for recurrent events. *Stat Med* 2006; 25:165-79; Jahn-Eimermacher A, Comparison of the Andersen-Gill model with Poisson and negative binomial regression on recurrent event data. *Comput Stat Data Anal* 2008; 52:4989-97).

An interim analysis was performed after 50% of the primary end-point events had been positively adjudicated. The prespecified stopping rule for efficacy was based on the Lan-DeMets procedure with the O'Brien-Fleming alpha-spending function. After review of the interim results, the data and safety monitoring board recommended that the trial should continue as planned.

To account for this interim analysis, the statistical significance level was set to 0.0490 for the final analysis of the primary end point. All other statistical tests were two-sided and conducted at the 0.05 significance level. Statistical analyses were performed with the use of SAS software, version 9.4 (SAS Institute). There was no prespecified plan to adjust for multiple comparisons across the multiple methods that were used to analyze the primary and secondary end points; results of these analyses are reported with point estimates and 95% confidence intervals, without P values. The 95% confidence intervals were not adjusted for multiple comparisons, and inferences drawn from them may not be reproducible. The final amendment to the statistical analysis plan was approved on Aug. 28, 2019, before unblinding of the trial-group assignments occurred.

Patients

Trial enrollment began in December 2015 and was completed in August 2018; the last trial visit was in July 2019. A total of 4745 patients under went randomization (with 2366 being assigned to the colchicine group and 2379 to the placebo group) and were followed for a median of 22.6 months. At the time of the database lock on Aug. 28, 2019, and unblinding on Aug. 29, 2019, vital status was available for all except 23 patients (9.5%); 89 patients (1.9%) were lost to follow-up, and 30 patients (0.6%) withdrew consent.

The characteristics of the patients at baseline are showing in Table 10.

TABLE 10

Characteristics of the Patients

| Characteristic | Colchicine (N = 2366) | Placebo (N = 2379) |
|---|---|---|
| Age-yr | 60.6 ± 10.7 | 60.5 ± 10.6 |
| Female sex-no. (%) | 472 (19.9) | 437 (18.4) |
| White race-no/total no. (%)† | 1350/1850 (73.0) | 1329/1844 (72.1) |
| Body-mass index | 28.2 ± 4.8 | 28.4 ± 4.7 |
| Current smoking-no./ total no. (%) | 708/2366 (29.9) | 708/2377 (29.8) |
| Hypertension-no. (%) | 1185 (50.1) | 1236 (52.0) |
| Diabetes-no. (%) | 462 (19.5) | 497 (20.9) |
| History of myocardial infarction-no. (%) | 370 (15.6) | 397 (16.7) |
| History of PCI-no. (%) | 392 (16.6) | 406 (17.1) |
| History of CABG-no. (%) | 69 (2.9) | 81 (3.4) |
| History of heart failure-no. (%) | 48 (2.0) | 42 (1.8) |
| History of stroke or TIA-no. (%) | 55 (2.3) | 67 (2.8) |
| Time from index myocardial infarction to randomization-days | 13.4 ± 10.2 | 13.5 ± 10.1 |
| PCI for index myocardial infarction-no./total no. (%) | 2192/2364 (92.7) | 2216/2375 (93.3) |
| Medication use-no. (%) | | |
| Aspirin | 2334 (98.6) | 2352 (98.9) |
| Other antiplatelet agent | 2310 (97.6) | 2337 (98.2) |
| Statin | 2339 (98.9) | 2357 (99.1) |
| Beta-blocker | 2116 (89.4) | 2101 (88.3) |

*Plus-minus values are means ± SD. Data were missing on the following characteristics: age (assessed according to date of birth; see below), for 435 patients; body-mass index (the weight in kilograms divided by the square of the height in meters), for 5; and information about the index myocardial infarction, for 6. Date of birth and race were not required fields because both were considered in some countries to be sensitive data that could allow for the identification of patients. For statistical reporting, missing information regarding the day of birth was replaced by 15, and missing information regarding the month and day of birth was replaced by July 1. CABG denotes coronary-artery bypass graft surgery, PCI percutaneous coronary intervention, and TIA transient ischemic attack.
†Race was reported by the patient.

Patients were enrolled a mean of 13.5 days after myocardial infarction. The mean age of the patients was 60.6 years, 19.2% of the patients were women, and 20.2% had diabetes. Most patients (93.0%) underwent percutaneous coronary intervention for their index myocardial infarction. Aspirin, a different antiplatelet agent, and a statin were taken by 98.8%, 97.9% and 99.0% of the patients, respectively.

At the end of the trial, the trial regimen had been discontinued in 18.4% of the patients in the colchicine group and in 18.7% of those in the placebo group. Among the patients who discontinued the trial regimen, the median time of taking the trial drug was 7.1 months (interquartile range, 1.9 to 14.6) in the colchicine group, as compared with 6.1 months (interquartile range, 1.6 to 14.4) in the placebo group. Overall, the median duration of receipt of the trial drug was 19.6 months in the colchicine group and 19.5 months in the placebo group.

Clinical Efficacy End Points

A primary end-point event occurred in 5.5% of the patients in the colchicine group, as compared with 7.1% of those in the placebo group (hazard ratio, 0.77; 95% confidence interval [CI], 0.61 to 0.96; P=0.02 by the log-rank test). A multivariable Cox regression model with adjustment for baseline covariates yielded a similar result (Table 11).

TABLE 11

Multivariable Cox Regression Model for Time to First Primary Endpoint.

| Effect | | Adjusted Hazard Ratio (95% CI) | P Value |
|---|---|---|---|
| Randomized treatment group | Colchicine vs. Placebo | 0.78 (0.62-0.98) | 0.03 |
| Age at randomization (years) | | 1.02 (1.01-1.03) | <0.001 |
| History of diabetes | Yes vs. No | 1.86 (1.46-2.37) | <0.001 |
| Prior coronary revascularization (PCI or CABG) | Yes vs. No | 2.02 (1.58-2.58) | <0.001 |
| Prior heart failure | Yes vs. No | 1.81 (1.08-3.04) | 0.03 |

CABG denotes coronary artery bypass graft, and PCI percutaneous coronary intervention.
The model was based on 4745 observations. All baseline characteristics that showed an association (P<0.20) with the occurrence of a first positively adjudicated primary endpoint were included in the stepwise multivariable Cox regression. For age at randomization, the hazard ratio is for an increase of one year of age.
In the prespecified per-protocol analysis involving patients who adhered to the protocol, the primary end point occurred in 5.1% of the patients in the colchicine group and in 7.1% of those in the placebo group (hazard ratio, 0.71; 95% CI, 0.56 to 0.90) (Table 12).

TABLE 12

Rates and Hazard Ratios for the Primary Endpoint and its Components in the Per-Protocol Population†.

| Clinical Outcome | Colchicine | Placebo | Hazard Ratio (95% CI) |
|---|---|---|---|
| Per-protocol population | N = 2260 | N = 2270 | |
| Primary endpoint-no. (%) | 115 (5.1%) | 162 (7.1%) | 0.71 (0.56-0.90) |
| CV death-no. (%) | 19 (0.8%) | 23 (1.0%) | 0.83 (0.45-1.53) |
| Resuscitated cardiac arrest-no. (%) | 5 (0.2%) | 5 (0.2%) | 1.00 (0.29-3.46) |
| MI-no. (%) | 77 (3.4%) | 92 (4.1%) | 0.84 (0.62-1.14) |
| Stroke-no. (%) | 5 (0.2%) | 19 (0.8%) | 0.26 (0.10-0.71) |
| Urgent hospitalization for angina requiring revascularization-no. (%) | 22 (1.0%) | 47 (2.1%) | 0.47 (0.28-0.78) |

CV denotes cardiovascular, and MI myocardial infarction.
†The per-protocol population consisted of patients without major protocol deviations.

Table 13 shows the percentages of patients with events and the hazard ratios for the components of the primary end point, including death from cardiovascular causes (hazard ratio, 0.84; 95% CI, 0.46 to 1.52), resuscitated cardiac arrest (hazard ratio, 0.83; 95% CI, 0.25 to 2.73), myocardial infarction (hazard ratio, 0.91; 95% CI, 0.68 to 1.21), stroke (hazard ratio, 0.26; 95% C, 0.10 to 0.70), and urgent hospitalization for angina leading to coronary revascularization (hazard ratio, 0.50; 95% C, 0.31 to 0.81). The hazard ratios remained unchanged in the analysis that took competing events into account.

TABLE 13

Major Clinical End-points (Intention-to-Treat Population)

| End Point | Colchicine (N = 2366) | Placebo (N = 2379) | Hazard Ratio (95% CI) | P Value |
|---|---|---|---|---|
| | number (percent) | | | |
| Primary composite end point | 131 (5.5) | 170 (7.1) | 0.77 (0.61-0.96) | 0.02† |
| Components of primary end point | | | | |
| Death from cardiovascular causes | 20 (0.8) | 24 (1.0) | 0.84 (0.46-1.52) | |
| Resuscitated cardiac arrest | 5 (0.2) | 6 (0.3) | 0.83 (0.25-2.73) | |
| Myocardial infarction | 89 (3.8) | 98 (4.1) | 0.91 (0.68-1.21) | |
| Stroke | 5 (0.2) | 19 (0.8) | 0.26 (0.10-0.70) | |
| Urgent hospitalization for angina leading to revascularization | 25 (1.1) | 50 (2.1) | 0.50 (0.31.-0.81) | |
| Secondary composite end point‡ | 111 (4.7) | 130 (5.5) | 0.85 (0.66-1.10) | |
| Death | 43 (1.8) | 44 (1.8) | 0.98 (0.64-1.49) | |
| Deep venous thrombosis or pulmonary embolus | 10 (0.4) | 7 (0.3) | 1.43 (0.54-3.75) | |
| Atrial fibrillation | 36 (1.5) | 40 (1.7) | 0.93 (0.59-1.46) | |

* Only the initial event was counted in the analyses of time to first event for the primary composite end point and for the secondary composite end point. In the component analysis, all events (first and subsequent) were counted separately.

†The log-rank test and the multivariable Cox proportional-hazards model (including age, history of diabetes, previous coronary revascularization, and previous heart failure yielded similar P values.

‡The secondary composite end point included death from cardiovascular causes, resuscitated cardiac arrest, myocardial infarction, and stroke.

The secondary efficacy end point consisting of a composite of death from cardiovascular causes, cardiac arrest, myocardial infarction, or stroke occurred in 4.7% of the patients in the colchicine group and in 5.5% of those in the placebo group (hazard ratio, 0.85; 95% CI, 0.66 to 1.10). Data on the primary, secondary, and exploratory efficacy end points are provided in Table 13. Two patients had a first positively adjudicated event of urgent hospitalization for angina leading to coronary revascularization within 14 days after randomization. The median time to this clinical end point was 258 days.

Efficacy results in prespecified subgroups are shown in Table 14. The total number of primary end-point events (first and recurrent) was 154 in the colchicine group and 223 in the placebo group, over periods of 52,949 and 53,060 patient-months of follow-up, respectively. Thus, the primary end-point event rates per 100 patient-months were 029 in the colchicine group and 0.42 in the placebo group (rate ratio, 0.66; 95% CI, 0.51 to 0.86) (Table 15).

TABLE 14

Primary Efficacy Composite Endpoint in Prespecified Subgroups†.

| Subgroup | Colchicine | Placebo | Hazard ratio (95% CI) |
|---|---|---|---|
| | no. of patients with event/total no. of patients (%) | | |
| All patients | 131/2366 (5.5%) | 170/2379 (7.1%) | 0.77 (0.61-0.96) |
| Smoking | | | |
| Non-smoker | 47/787 (6.0%) | 52/797 (6.5%) | 0.90 (0.61; 1.34) |
| Previous smoker | 46/871 (5.3%) | 77/872 (8.8%) | 0.59 (0.41; 0.85) |
| Active smoker | 38/708 (5.4%) | 41/708 (5.8%) | 0.93 (0.60; 1.44) |
| History of diabetes | | | |
| Yes | 40/462 (8.7%) | 65/497 (13.1%) | 0.65 (0.44; 0.96) |
| No | 91/1904 (4.8%) | 105/1882 (5.6%) | 0.85 (0.64; 1.13) |
| History of hypertension | | | |
| Yes | 83/1185 (7.0%) | 112/1236 (9.1%) | 0.76 (0.57; 1.01) |
| No | 48/1181 (4.1%) | 58/1143 (5.1%) | 0.80 (0.54; 1.17) |
| Prior MI | | | |
| Yes | 46/370 (12.4%) | 47/397 (11.8%) | 1.05 (0.70; 1.58) |
| No | 85/1996 (4.3%) | 123/1982 (6.2%) | 0.68 (0.51; 0.89) |
| Prior PCI or CABG | | | |
| Yes | 48/419 (11.5%) | 57/447 (12.8%) | 0.91 (0.62; 1.34) |
| No | 83/1947 (4.3%) | 113/1932 (5.8%) | 0.72 (0.54; 0.95) |
| Prior stroke or TIA | | | |
| Yes | 8/55 (14.5%) | 9/67 (13.4%) | 1.09 (0.42; 2.82) |
| No | 123/2311 (5.3%) | 161/2312 (7.0%) | 0.76 (0.60; 0.96) |
| Sex‡ | | | |
| Male | 94/1894 (5.0%) | 135/1942 (7.0%) | 0.70 (0.54; 0.91) |
| Female | 37/472 (7.8%) | 35/437 (8.0%) | 0.99 (0.63; 1.58) |
| White blood cell count¶ | | | |
| Below median | 41/660 (6.2%) | 46/637 (7.2%) | 0.85 (0.56; 1.29) |
| Above median | 34/637 (5.3%) | 44/664 (6.6%) | 0.80 (0.51; 1.25) |

CABG denotes coronary artery bypass graft, MI myocardial infarction, PCI percutaneous coronary intervention, and TIA transient ischemic attack.
†The final amendment to the statistical analysis plan, which listed the subgroups of interest, was approved on Aug. 28, 2019 and unblinding occurred on Aug. 29, 2019.
‡The hazard ratio for the primary endpoint was 0.70 (0.52; 0.93) in men and 0.81 (0.47; 1.41) in women in the per-protocol population.
The median value for total white blood cell count was $8.64 \times 10^3/\mu L$.

TABLE 15

Total (First and Recurrent) Primary Endpoint Events.

| Total Primary Endpoint Events | | Colchicine (N = 2366) | Placebo (N = 2379) |
|---|---|---|---|
| Number of primary endpoint events per patient | 0 | 2235 | 2209 |
| | 1 | 111 | 132 |
| | 2 | 18 | 26 |
| | 3 | 1 | 9 |
| | 4 | 1 | 3 |
| Total number of primary endpoint events | | 154 | 223 |
| Total follow-up months | | 52949 | 53060 |
| Rate of primary endpoint events per 100 patient-months | | 0.29 | 0.42 |

| | | Hazard Ratio or Rate Ratio (95% CI) |
|---|---|---|
| Negative binomial model† | | 0.66 (0.51; 0.86) |
| Andersen-Gill models‡ | | 0.69 (0.54; 0.88) |
| WLW model¶ | $1^{st}$ Event | 0.77 (0.61; 0.96) |
| | $2^{nd}$ Event | 0.73 (0.48; 1.11) |
| | $3^{rd}$ Event | 0.64 (0.37; 1.10) |
| | Average | 0.77 (0.61; 0.96) |

WLW denotes Wei-Lin-Weissfeld method.
†The negative binomial regression model was used to calculate marginal rate ratio.
‡The Andersen-Gill model was used with a robust variance estimator (sandwich estimator) to calculate hazard ratio.

Regarding Table 15, the Wei-Lin-Weissfeld marginal model was used to calculate hazard ratios for the time to the first, second and third event as well as the weighted average of these hazard ratios. To account for the occurrence of multiple primary endpoint events within patients, recurrent event analyses were undertaken using three statistical approaches as there is no strong consensus as to which method is preferable. First, a negative binomial regression model was used with the number of events as the outcome and the length of follow-up time in months as an offset term (Hansson G K. Inflammation, atherosclerosis, and coronary artery disease. *N Engl J Med* 2005; 352:1685-95). Marginal rate ratio was provided, along with 95% confidence interval. The Andersen and Gill model (Ridker P M, et al., Antiinflammatory therapy with canakinumab for atherosclerotic disease. *N Engl J Med* 2017; 377:1119-31) with a robust variance estimator (Ridker P M et al., Low-dose methotrexate for the prevention of atherosclerotic events. *N Engl J Med* 2019; 380:752-62; and Ravelli R B et al., Insight into tubulin regulation from a complex with colchicine and a stathmin-like domain. *Nature* 2004; 428:198-202) was utilized to account for the dependency of within-patient events based on a gap-time approach considering the time since a previous event. The Andersen-Gill model is a simple extension of the Cox model based on all events of all patients and estimates a hazard ratio assuming that the instantaneous risk of experiencing an event is the same irrespective of whether previous events occurred. Results from these two models are often similar (Perico N et al., Colchicine interferes with L-selectin and leukocyte function-associated antigen-1 expression on human T lymphocytes and inhibits T cell activation. *J Am Soc Nephrol* 1996; 7:594-601; and Pope R M and Tschopp J, The role of interleukin-1 and the inflammasome in gout: implications for therapy. *Arthritis Rheum* 2007; 56:3183-8). Finally, an approach based on the Wei, Lin and Weissfeld marginal model was conducted whereby times from randomization to first, second and subsequent event were modeled with a Cox proportional hazards model that used a covariance matrix estimate for the regression coefficients that accounted for the possible intra-patient correlation (Cerquaglia C et al., Pharmacological and clinical basis of treatment of Familial Mediterranean Fever (FMF) with colchicine or analogues: an update. *Curr Drug Targets Inflamm Allergy* 2005; 4:117-24; Imazio M et al., Colchicine in addition to conventional therapy for acute pericarditis: results of the COlchicine for acute PEricarditis (COPE) trial. *Circulation* 2005; 112:2012-6; and Nidorf S M et al., Low-dose colchicine for secondary prevention of cardiovascular disease. *J Am Coll Cardiol* 2013; 61:404-10). This approach assumes that all patients are at risk for any event since randomization. Marginal hazard ratios for a $k^{th}$ event (i.e. based on time from randomization to $k^{th}$ event), as well as a weighted average of these hazard ratios, were provided along with 95% confidence intervals. It has been argued that this approach preserves the randomization and permits valid treatment effect estimation (Fine J P and Gray R J, A proportional hazards model for the subdistribution of a competing risk. *J Am Stat Assoc* 1999; 94:496-509).

Biomarkers of Inflammation

High-sensitivity C-reactive protein was measured in a subgroup of only 207 patients at the time of randomization and 6 months later, and the median concentration at trial entry was 4.28 mg per liter. The baseline characteristics of these patients were similar to those of the overall population (Table 16), but the small and selected subgroup with these data limits the interpretation of these analyses. The adjusted geometric mean percent changes in the high-sensitivity C-reactive protein level at 6 months after myocardial infarction were −70.0% in the colchicine group and −66.6% in the placebo group, and the placebo-adjusted geometric mean percent change was −10.1% percentage points in the colchicine group (95% CI, −28.6 to 13.4) (Table 17).

TABLE 16

Characteristics of the Trial Patients with hs-CRP data values.

| Characteristic | Colchicine (N = 99) | Placebo (N = 108) |
|---|---|---|
| Age-years | 62.1 ± 9.7 | 61.2 ± 10.2 |
| Female sex-no. (%) | 18 (18.2%) | 14 (13.0%) |
| Caucasian-no. (%) | 91 (93.8%) | 89 (89.0%) |
| Body-mass index (kg/m$^2$) | 28.8 ± 4.5 | 29.1 ± 4.2 |
| Smoking-no. (%) | 20 (20.2%) | 20 (18.5%) |
| Hypertension-no. (%) | 44 (44.4%) | 62 (57.4%) |
| Diabetes-no. (%) | 12 (12.1%) | 15 (13.9%) |
| Prior MI-no. (%) | 14 (14.1%) | 16 (14.8%) |
| Prior PCI-no. (%) | 24 (24.2%) | 21 (19.4%) |
| Prior CABG-no. (%) | 4 (4.0%) | 6 (5.6%) |
| Prior heart failure-no. (%) | 4 (4.0%) | 1 (0.9%) |
| Prior stroke/TIA-no. (%) | 1 (1.0%) | 2 (1.9%) |
| Index MI to randomization-days | 17.0 ± 9.2 | 15.8 ± 9.8 |
| PCI for index MI-no. (%) | 93 (93.9%) | 104 (96.3%) |
| Aspirin use-no. (%) | 98 (99.0%) | 106 (98.1%) |
| Other anti-platelet agent-no. (%) | 98 (99.0%) | 108 (100%) |
| Statin use-no. (%) | 99 (100%) | 107 (99.1%) |
| Beta-blocker-no. (%) | 83 (83.8%) | 86 (79.6%) |

CABG denotes coronary artery bypass graft surgery, MI myocardial infarction, PCI percutaneous coronary intervention, and TIA transient ischemic attack.

TABLE 17

Biomarkers of Inflammation.

| Biomarker | Colchicine | Placebo |
|---|---|---|
| Hs-C reactive protein (mg/L) | N = 99 | N = 108 |
| Randomization, geometric mean (IQR)† | 4.27 (2.12, 7.22) | 5.09 (2.45, 11.96) |
| 6 months, geometric mean (IQR) | 1.37 (0.75, 2.13) | 1.60 (0.90, 2.65) |
| Adjusted GM percent change (95% CI)‡ | −70.0 (−74.6, −64.5) | −66.6 (−71.5, −60.8) |
| Placebo-adjusted GM percent change (95% CI)¶ | −10.1 (−28.6, 13.4) | — |
| Total white blood cell count ($10^3/\mu L$) | N = 992 | N = 980 |
| Randomization, geometric mean (IQR)† | 8.54 (7.10, 10.40) | 8.63 (7.20, 10.70) |
| 12 months, geometric mean (IQR) | 6.95 (5.99, 8.30) | 7.03 (5.96, 8.48) |
| Adjusted GM percent change (95% CI)‡ | −18.81 (−20.12, −17.47) | −19.02 (−20.46, −17.55) |
| Placebo-adjusted GM percent change (95% CI)¶ | 0.26 (−2.15, 2.72) | — |
| Circulating lymphocytes ($10^3/\mu L$) | | |
| Randomization, geometric mean (IQR)† | 1.79 (1.40, 2.40) | 1.79 (1.42, 2.46) |
| 12 months, geometric mean (IQR) | 1.83 (1.50, 2.44) | 1.82 (1.50, 2.44) |
| Adjusted GM percent change (95% CI)‡ | 1.80 (−0.46, 4.11) | 0.69 (−1.54, 2.98) |
| Placebo-adjusted GM percent change (95% CI)¶ | 1.10 (−2.06, 4.36) | — |
| Circulating neutrophils ($10^3/\mu L$) | | |
| Randomization, geometric mean (IQR)† | 5.45 (4.36, 7.15) | 5.47 (4.30, 7.46) |
| 12 months, geometric mean (IQR) | 3.95 (3.27, 5.08) | 3.99 (3.34, 5.20) |
| Adjusted GM percent change (95% CI)‡ | −27.63 (−29.48, −25.73) | −27.95 (−29.91, −25.93) |
| Placebo-adjusted GM percent change (95% CI)¶ | 0.45 (−3.28, 4.32) | — |

GM denotes geometric mean, HS high-sensitivity, and IQR inter-quartile range.
†The geometric mean was obtained by exponentiating the mean of log-transformed data.
‡The adjusted geometric mean percent change was obtained by exponentiating the adjusted mean from the analysis of covariance model (based on log-transformed data), then subtracting 1 and multiplying by 100. The bounds of the 95% confidence intervals were obtained similarly.

In Table 17, the placebo-adjusted geometric mean percent change was obtained by exponentiating the adjusted mean difference between groups from the analysis of covariance model (based on log-transformed data), then subtracting 1 and multiplying by 100.

In addition, the C-reactive protein biomarker sub-study was implemented following a protocol amendment and was optional for sites and for patients; 34 sites accepted to participate in this substudy. There were 213 and 208 patients who provided blood samples at baseline and 6 months, respectively. Paired baseline and 6-month hs-CRP values were available in 207 patients. Clinically available white blood cell counts were obtained from 2598 patients at baseline and 1998 patients at 12 months, and paired baseline and 12-month values were available in 1972 patients. Statistical analysis was conducted on the patients who provided both baseline and follow-up data and as these were exploratory analyses, no missing data was imputed.

Information about white-cell counts at baseline and at the 12-month follow-up were also available for relatively small subgroup of 1972 patients. The adjusted geometric mean percent changes from baseline to 1 year in the total white-cell count were −18.8% in the colchicine group and −19.0% in the placebo group, with no significant difference between groups (0.3% percentage points; 95% CI, −2.2 to 2.7).

Safety and Adverse Events

The incidence of adverse events that were considered to be related to trial drug was 16.0% in the colchicine group and 15.8% in the placebo group, and the overall incidence of serious adverse events was 16.4% and 17.2%, respectively (Table 18).

TABLE 18

Adverse Events (Safety Population)

| Event | Colchicine (N = 2330) number of patients (percent) | Placebo (N = 2346) number of patients (percent) | P Value |
|---|---|---|---|
| Any related adverse event† | 372 (16.0) | 371 (15.8) | 0.89 |
| Any serious adverse event‡ | 383 (16.4) | 404 (17.2) | 0.47 |
| Gastrointestinal adverse event | 408 (17.5) | 414 (17.6) | 0.90 |
| Gastrointestinal serious adverse event | 46 (2.0) | 36 (1.5) | 0.25 |
| Diarrhea adverse event | 225 (9.7) | 208 (8.9) | 0.35 |
| Nausea adverse event | 43 (1.8) | 24 (1.0) | 0.02 |
| Flatulence adverse event | 15 (0.6) | 5 (0.2) | 0.02 |
| Gastrointestinal hemorrhage | 7 (0.3) | 5 (0.2) | 0.56 |
| Infection serious adverse event | 51 (2.2) | 38 (1.6) | 0.15 |
| Pneumonia serious adverse event | 21 (0.9) | 9 (0.4) | 0.03 |
| Septic shock serious adverse event | 2 (0.1) | 2 (0.1) | 0.99 |
| Hospitalization for heart failure | 25 (1.1) | 17 (0.7) | 0.21 |
| Cancer§ | 43 (1.8) | 46 (2.0) | 0.77 |
| Anemia | 14 (0.6) | 10 (0.4) | 0.40 |
| Leukopenia | 2 (0.1) | 3 (0.1) | 0.66 |
| Thrombocytopenia | 3 (0.1) | 7 (0.3) | 0.21 |

*The safety population was defined as patients who took at least one dose of colchicine or placebo. All serious adverse events were recorded, and the only other adverse events recorded were those that were related to the gastrointestinal system, events that were judged by the investigator to be related to colchicine or placebo, or laboratory abnormalities that were judged by the investigator to be clinically significant. This table lists serious adverse events that were present in more than 2% of the patients in either trial group, adverse events that were considered to be related to colchicine or placebo in more than 5% of the patients in either trial group, and any other safety events of special interest. Chi-square tests were conducted to compare the incidence of adverse events between the trial groups.
†These adverse events were considered to be related to colchicine or placebo by the physician in charge of the participant.
‡There was one serious adverse event of myopathy, which was attributed to high-dose statin therapy (rosuvastatin at a dose of 40 mg daily) by the local investigator and academic sponsor, in a man of short stature (165 cm, 68 kg) with normal renal function in the colchicine group who had received colchicine for 8 days 3 months before the adverse event.
§Cancers, excluding nonmelanoma skin cancers, occurred in 42 patients (1.8%) in the colchicine group and in 44 (1.9%) in the placebo group.

At least one gastrointestinal adverse event during the double-blind period occurred in 17.5% of the patients in the colchicine group, as compared with 17.6% of those in the placebo group. Diarrhea was reported in 9.7% of the patients in the colchicine group and in 8.9% of those in the placebo group (P=0.35), and nausea was more common in the colchicine group than in the placebo group (1.8% vs. 1.0%, P=0.02). Pneumonia was reported as a serious adverse event in 0.9% of the patients in the colchicine group, as compared with 0.4% of those in the placebo group (P=0.03).

In COLCOT, the risk of the primary composite efficacy end point of death from cardiovascular causes, resuscitated cardiac arrest, myocardial infarction, stroke, or urgent hospitalization for angina leading to coronary revascularization, as assessed in a time-to-event analysis, was significantly lower among the patients who were randomly assigned to receive 0.5 mg of colchicine once daily than among those who received placebo. This result was due predominantly to a lower incidence of strokes and urgent hospitalizations for angina leading to coronary revascularization.

These results were observed against a background of appropriate medications, which included aspirin, a different antiplatelet agent, and a statin in 98 to 99% of the patients. In addition, percutaneous coronary intervention was performed in 93% of the patients for their index myocardial infarction. The benefits of colchicine with regard to cardiovascular end points in COLCOT were at least as large as those of canakinumab in CANTOS (Ridker P M et al., Antiinflammatory therapy with canakinumab for atherosclerotic disease. *N Engl J Med* 2017; 377:1119-31). In the small subgroup of patients with available data, a large (>65%) reduction in the C-reactive protein level occurred over the first 6 months after myocardial infarction in both trial groups in COLCOT, but the difference between the changes in the groups was not significant. These findings must be interpreted cautiously given that this was a small subgroup that was not randomly selected from the full trial sample. A similar observation was made with white-cell counts. The different patient populations involved in the two trials—early after myocardial infarction in COLCOT and stable coronary disease in CANTOS—may also have affected the relationship between biomarkers of inflammation and the effects of treatments on ischemic end points.

The known benefits of colchicine in the treatment of pericarditis were not at play in COLCOT.

Postinfarction pericarditis typically occurs within the first few days after the injury, whereas the mean time from the index myocardial infarction to randomization was 13.5 days. There were only two patients with a first positively adjudicated event of urgent hospitalization for angina leading to coronary revascularization within 14 days after randomization, and the median time to this clinical end point was 258 days.

The most common adverse events observed were gastrointestinal. Diarrhea was reported in 9.7% of the patients in the colchicine group and in 8.9% of those in the placebo group, and nausea occurred in 1.8% and 1.0%, respectively. Infection as a serious adverse event was more frequent in the colchicine group than in the placebo group (in 2.2% vs. 1.6% of the patients), and pneumonia as a serious adverse event was also more frequent in the colchicine group (0.9% vs. 0.4%). These differences in the incidence of infections could be due to the play of chance or could reflect altered immunologic responses.

In contrast to canakinumab (Ridker P M et al., Antiinflammatory therapy with canakinumab for atherosclerotic disease. *N Engl J Med* 2017; 377:1119-31), colchicine did not increase the incidence of septic shock in our trial. Infections have previously been described in patients who have attempted suicide by taking an overdose of colchicine (Kocak Z et al., Colchicine intoxication and infection risk: a case report. *J Clin Pharm Ther* 2008; 33:451-2). There was no serious adverse event of myopathy linked to colchicine despite the use of statins in 99% of the patients in the trial.

In conclusion, among patients with a recent myocardial infarction, colchicine at a dose of 0.5 mg daily led to a significantly lower percentage of patients with ischemic cardiovascular events than placebo.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Some embodiments of the invention are within the following numbered paragraphs.

1. A method of treating a patient after having a myocardial infarction (MI), the method comprising initiating the administration of colchicine at a daily low dose to the patient within about 3 days of the MI.

2. A method of treating a patient after having a myocardial infarction (MI), the method comprising initiating the administration of colchicine at a daily low dose to the patient within about 4 days of the MI.

3. The method paragraph 1 or 2, wherein percutaneous coronary intervention was performed for treating the patient's MI.

4. The method of any one of paragraphs 1-3, wherein the patient was prescribed a medication.

5. The method according to paragraph 4, wherein the medication is an antiplatelet agent.

6. The method according to paragraph 4, wherein the medication is aspirin.

7. The method according to paragraph 4, wherein the medication is a statin.

8. The method according to any one of paragraphs 1-7, wherein the patient is at a lower risk of a cardiovascular event, relative to a patient not being administered colchicine.

9. The method according to paragraph 8, wherein the cardiovascular event is an ischemic cardiovascular event.

10. The method according to paragraph 8, wherein the cardiovascular event is cardiovascular death, resuscitated cardiac arrest, myocardial infarction, stroke, or urgent hospitalization for angina requiring coronary revascularization.

11. The method according to any one of paragraphs 1-10, wherein the patient has atherosclerotic coronary artery disease.

12. A method of reducing the risk of a stroke in a patient after having an M, the method comprising initiating the administration of colchicine at a daily low dose to the patient within about 30 days of the MI.

13. The method according to paragraph 12, wherein the method comprises administering colchicine within 4-7 days of the MI.

14. The method according to paragraph 12, wherein the method comprises administering colchicine within 3 days of the MI.

16. The method according to any one of paragraphs 1-15, wherein the administration of colchicine is initiated upon assessment in (a) an emergency department (ED), (b) the hospital, or (c) a medical office setting.

17. The method according to any one of paragraphs 1-16, wherein the colchicine is in the form of a tablet.

18. The method of paragraph 17, wherein the tablet is coated.

19. The method of paragraph 18, wherein the tablet is film-coated.

20. The method according to any one of paragraphs 1-19, wherein the colchicine is administered at 0.3 to 0.7 mg.

21. The method according to any one of paragraphs 1-20, wherein the colchicine is administered at 0.4 to 0.6 mg 22. The method according to paragraph 21, wherein the colchicine is administered at about 0.5 mg.

23. The method according to any one of paragraph 1-22, wherein the colchicine is administered once, twice or three times a day.

24. The method according to paragraph 23, wherein the colchicine is administered once per day.

25. The method of any one of paragraphs 1-24, wherein the colchicine is administered without pre-loading the patient with colchicine.

26. The method of any one of paragraphs 1-25, wherein the patient is an adult human.

Other embodiments are within the claims.

What is claimed is:

1. A method of treating a patient after having a myocardial infarction (MI), the method comprising initiating the administration of colchicine at a daily low dose to the patient within about 3 days of the MI, wherein the colchicine is administered without pre-loading the patient with a higher dose of colchicine before the administration at the daily low dose, wherein percutaneous coronary intervention was performed for treating the patient's MI.

2. The method according to claim 1, wherein the patient was prescribed a medication.

3. The method according to claim 2, wherein the medication is an antiplatelet agent.

4. The method according to claim 2, wherein the medication is aspirin.

5. The method according to claim 2, wherein the medication is a statin.

6. The method according to claim 1, wherein the patient is at a lower risk of a cardiovascular event, relative to a patient not being administered colchicine.

7. The method according to claim 6, wherein the cardiovascular event is an ischemic cardiovascular event.

8. A method of treating a patient after having a myocardial infarction (MI), the method comprising initiating the administration of colchicine at a daily low dose to the patient within about 3 days of the MI, wherein the colchicine is administered without pre-loading the patient with a higher dose of colchicine before the administration at the daily low dose, wherein the patient is at a lower risk of a cardiovascular event, relative to a patient not being administered colchicine, and wherein the cardiovascular event is resuscitated cardiac arrest, stroke, or urgent hospitalization for angina requiring coronary revascularization.

9. The method according to claim 6, wherein the cardiovascular event is myocardial infarction.

10. The method according to claim 8, wherein the cardiovascular event is stroke.

11. The method according to claim 8, wherein the cardiovascular event is urgent hospitalization for angina requiring coronary revascularization.

12. The method according to claim 1, wherein the patient has atherosclerotic coronary artery disease.

13. The method according to claim 1, wherein the administration of colchicine is initiated upon assessment in (a) an emergency department (ED), (b) the hospital, or (c) a medical office setting.

14. The method according to claim 1, wherein the colchicine is in the form of a tablet.

15. The method of claim 14, wherein the tablet is coated.

16. The method of claim 15, wherein the tablet is film-coated.

17. The method according to claim 1, wherein the colchicine is administered at 0.3 to 0.7 mg.

18. The method according to claim 17, wherein the colchicine is administered at 0.4 to 0.6 mg.

19. The method according to claim 18, wherein the colchicine is administered at 0.5 mg.

20. The method according to claim 8, wherein the colchicine is administered at 0.5 mg.

21. The method according to claim 9, wherein the colchicine is administered at 0.5 mg.

22. The method according to claim 10, wherein the colchicine is administered at 0.5 mg.

23. The method according to claim 11, wherein the colchicine is administered at 0.5 mg.

24. The method according to claim 1, wherein the colchicine is administered once, twice or three times a day.

25. The method according to claim 24, wherein the coichicine is administered once per day.

26. The method according to claim 1, wherein the patient is an adult human.

27. A method of reducing the risk of a stroke in a patient after having an MI, the method comprising initiating the administration of colchicine at a daily low dose to the patient within about 30 days of an MI.

28. The method according to claim 27, wherein the method comprises administering coichicine within 4 to 7 days of the MI.

29. The method according to claim 27, wherein the patient was prescribed a medication.

30. The method according to claim 29, wherein the medication is an antiplatelet agent.

31. The method according to claim 29, wherein the medication is aspirin.

32. The method according to claim 29, wherein the medication is a statin.

33. The method according to claim 27, wherein the patient has atherosclerotic coronary artery disease.

34. The method according to claim 27, wherein the coichicine is administered at 0.5 mg.

35. The method according to claim 27, wherein the colchicine is administered once per day.

36. The method according to claim 27, wherein the administration of colchicine is initiated upon assessment in (a) an emergency department (ED), (b) the hospital, or (c) a medical office setting.

37. The method according to claim 27, wherein the colchicine is in the form of a coated tablet.

38. The method of claim 37, wherein the tablet is film-coated.

39. The method of claim 27, wherein the patient is an adult human.

40. The method according to claim 8, wherein the patient was prescribed a medication.

41. The method according to claim 40, wherein the medication is an antiplatelet agent.

42. The method according to claim 40, wherein the medication is aspirin.

43. The method according to claim 40, wherein the medication is a statin.

44. The method according to claim 8, wherein the patient has atherosclerotic coronary artery disease.

45. The method according to claim 8, wherein the colchicine is administered once per day.

46. The method according to claim 8, wherein the administration of colchicine is initiated upon assessment in (a) an emergency department (ED), (b) the hospital, or (c) a medical office setting.

47. The method according to claim 8, wherein the colchicine is in the form of a coated tablet.

48. The method of claim 47, wherein the tablet is film-coated.

49. The method of claim 8, wherein the patient is an adult human.

50. The method of claim 8, wherein the cardiovascular event is resuscitated cardiac arrest.

* * * * *

UNITED STATES PATENT AND TRADEMARK OFFICE
CERTIFICATE OF CORRECTION

PATENT NO. : 11,400,063 B2
APPLICATION NO. : 17/097285
DATED : August 2, 2022
INVENTOR(S) : Jean-Claude Tardif It is certified that error appears in the above-identified patent and that said Letters Patent is hereby corrected as shown below:

In the Claims

Column 41, Line 50, replace "alter" with --after--.

Column 42, Line 30, replace "coichicine" with --colchicine--;
       Line 38, replace "coichicine" with --colchicine--;
       Line 51, replace "coichicine" with --colchicine--.

Signed and Sealed this
Twenty-fifth Day of October, 2022

Katherine Kelly Vidal
*Director of the United States Patent and Trademark Office*